US006054444A

United States Patent [19]
Jackson et al.

[11] Patent Number: 6,054,444
[45] Date of Patent: Apr. 25, 2000

[54] PHOSPHONIC ACID DERIVATIVES

[75] Inventors: Paul F. Jackson, Bel Air; Keith M. Maclin, Baltimore; Kevin L. Tays, Elkridge; Barbara S. Slusher, Kingsville, all of Md.

[73] Assignee: Guilford Pharmaceuticals Inc., Baltimore, Md.

[21] Appl. No.: 08/842,360

[22] Filed: Apr. 24, 1997

[51] Int. Cl.$^7$ .................. A61K 31/675; A61K 31/67; A61K 31/665; A61K 31/66; C07F 9/6553; C07F 9/655; C07F 9/58; C07F 9/572; C07F 9/40

[52] U.S. Cl. .................. 514/89; 514/80; 514/95; 514/99; 514/120; 514/114; 546/22; 546/25; 548/414; 549/6; 549/218; 549/222; 558/179; 562/24

[58] Field of Search .................. 514/89, 120; 546/22, 546/25; 558/179; 562/24

[56] References Cited

U.S. PATENT DOCUMENTS

| | | |
|---|---|---|
| H1312 | 5/1994 | Coughlin et al. |
| 4,052,160 | 10/1977 | Cook et al. ........................ 422/15 |
| 4,151,172 | 4/1979 | Ondetti et al. |
| 4,168,267 | 9/1979 | Petrillo, Jr. |
| 4,316,896 | 2/1982 | Thorsett et al. |
| 4,337,201 | 6/1982 | Petrillo, Jr. |
| 4,374,131 | 2/1983 | Petrillo, Jr. |
| 4,444,765 | 4/1984 | Karanewsky et al. |
| 4,448,772 | 5/1984 | Karanewsky . |
| 4,452,790 | 6/1984 | Karanewsky et al. |
| 4,452,791 | 6/1984 | Ryono et al. |
| 4,468,519 | 8/1984 | Krapcho . |
| 4,547,324 | 10/1985 | Wong et al. |
| 4,555,506 | 11/1985 | Karanewsky et al. |
| 4,560,680 | 12/1985 | Ryono et al. |
| 4,560,681 | 12/1985 | Karanewsky . |
| 4,567,166 | 1/1986 | Karanewsky et al. |
| 4,616,005 | 10/1986 | Karanewsky et al. |
| 4,671,958 | 6/1987 | Rodwell et al. |
| 4,703,043 | 10/1987 | Karanewsky et al. |
| 4,715,994 | 12/1987 | Parsons et al. |
| 4,716,155 | 12/1987 | Karanewsky et al. |
| 4,741,900 | 5/1988 | Alvarez et al. |
| 4,849,525 | 7/1989 | Weller, III et al. |
| 4,853,326 | 8/1989 | Quash et al. |
| 4,867,973 | 9/1989 | Goers et al. |
| 4,885,283 | 12/1989 | Broadhurst et al. |
| 4,906,779 | 3/1990 | Weber et al. |
| 4,918,064 | 4/1990 | Cordi et al. |
| 4,937,183 | 6/1990 | Ultee et al. |
| 4,950,738 | 8/1990 | King et al. |
| 4,959,493 | 9/1990 | Ohfume et al. |
| 4,962,097 | 10/1990 | Parsons et al. |
| 4,988,681 | 1/1991 | Ishikawa et al. |
| 4,994,446 | 2/1991 | Sokolovsky et al. |
| 5,030,732 | 7/1991 | Morita et al. |
| 5,041,644 | 8/1991 | Morita et al. |
| 5,047,227 | 9/1991 | Rodwell et al. |
| 5,061,806 | 10/1991 | Morita et al. |
| 5,093,525 | 3/1992 | Weber et al. |
| 5,099,063 | 3/1992 | Parsons et al. |
| 5,136,080 | 8/1992 | Miller et al. |

(List continued on next page.)

FOREIGN PATENT DOCUMENTS

| | | |
|---|---|---|
| 4118 | 5/1966 | France . |
| 2308634 | 11/1976 | France . |
| 2318943 | 2/1977 | France . |
| 3142517 | 5/1983 | Germany . |
| WO 96/26272 | 8/1996 | WIPO . |
| WO 97/48399 | 12/1997 | WIPO . |
| WO 98/13044 | 4/1998 | WIPO . |

OTHER PUBLICATIONS

Vornov, James J., "Toxic NMDA–Receptor Activation Occurs During Recovery in a Tissue Culture Model of Ischemia," *J. of Neurochemistry*, (1995) 65:4, 1681–1691.

Slusher, Barbara S. et al., "Rat Brain N–Acetylated α–Linked Acidic Dipeptidase Activity," *J. of Biological Chemistry*, (1990) 265:34, 21297–21301.

Slusher, Barbara S. et al., "Immunocytochemical Localization of the N–Acetyl–Aspartyl–Glutamide (NAAG) Hydrolyzing Enzyme N–Acetylated α–Linked Acidic Dipeptidase (NAALADase)," *J. of Comparative Neurology*, (1992) 315, 217–229.

Slusher, Barbara S., "NAALADase: A Potential Regulator of Synaptic Glutamate," *Biotech Update DuPont NEN*, (1994) 9:2, 37–39.

Jackson, Paul F. et al., "Design, Synthesis, and Biological Activity of a Potent Inhibitor of the Neuropeptidase N–Acetylated α–Linked Acidic Dipeptidase," *J. of Medicinal Chemistry*, (1995) 39:2, 619–622.

Carter, Ruth E. et al., "Prostate–specific membrane antigen is a hydrolase with substrate and pharmacologic characteristics of a neuropeptidase," *Proc. Natl. Acad. Sci. USA*, (1996) 93, 749–753.

Heston, W.D.W., "Potential Uses of Prostate Specific Membrane Antigen (PMSA) : a Neurocarboxypeptidase and Membrane Folate Hydrolase," *Urologe [A]*, v. 35, pp. 400–407 (1996).

Hurn, P., "Gender–Linked Injury After Focal Cerebral Ischemia," *Society for Neuroscience 1996 Abstract Form*, (1996).

Bhardwaj, A., "Striatal Nitric Oxide (NO) Production is Enhanced In Focal Cerebral Ischemia: An In Vivo Microdialysis Study," *Society for Neuroscience 1996 Abstract Form*, (1996).

(List continued on next page.)

*Primary Examiner*—Michael G. Ambrose
*Attorney, Agent, or Firm*—Gary M. Nath; Suet M. Chong; Nath & Associates

[57] ABSTRACT

The present invention relates to phosphonic acid derivatives that inhibit N-Acetylated α-Linked Acidic Dipeptidase (NAALADase) enzyme activity, pharmaceutical compositions comprising such derivatives, and methods of using such derivatives to inhibit NAALADase activity, to treat a glutamate abnormality and to treat a prostate disease in an animal.

33 Claims, 7 Drawing Sheets

U.S. PATENT DOCUMENTS

| | | |
|---|---|---|
| 5,140,104 | 8/1992 | Coughlin et al. . |
| 5,143,908 | 9/1992 | Parsons et al. . |
| 5,145,990 | 9/1992 | Parsons et al. . |
| 5,147,867 | 9/1992 | Parsons et al. . |
| 5,156,840 | 10/1992 | Goers et al. . |
| 5,162,504 | 11/1992 | Horoszewicz . |
| 5,162,512 | 11/1992 | King et al. . |
| 5,190,976 | 3/1993 | Weber et al. . |
| 5,196,510 | 3/1993 | Rodwell et al. . |
| 5,242,915 | 9/1993 | Ueda et al. . |
| 5,262,568 | 11/1993 | Weber et al. . |
| 5,326,856 | 7/1994 | Coughlin et al. . |
| 5,336,689 | 8/1994 | Weber et al. . |
| 5,449,761 | 9/1995 | Belinka, Jr. et al. . |
| 5,474,547 | 12/1995 | Aebischer et al. . |
| 5,489,525 | 2/1996 | Pastan . |
| 5,495,042 | 2/1996 | Belinka, Jr. et al. . |
| 5,500,420 | 3/1996 | Maiese . |
| 5,508,273 | 4/1996 | Beers et al. . |
| 5,527,885 | 6/1996 | Coughlin et al. . |
| 5,538,866 | 7/1996 | Israeli et al. . |
| 5,538,957 | 7/1996 | Tsaklakidis et al. . |
| 5,594,007 | 1/1997 | Chenard . |

OTHER PUBLICATIONS

Stauch, Barbara L. et al., "The effects of N–acetylated alpha–linked acidic dipeptidase (NAALADase) inhibitors on [$^3$H]NAAG catabolism in vivo," *Neuroscience Letters,* (1989) 100, 295–300.

Meyerhoff, James L. et al., "Activity of a NAAG–hydrolizing enzyme in brain may affect seizure susceptibility in genetically epilepsy–prone rats," *Molecular Neurobiology of Epilepsy,* (1992) Chap. 16, 163–172.

Subasinghe, N. et al., "Synthesis of acylic and dehydroaspartic acid analogues of Ac–Asp–Glu–OH and their inhibition of rat brain N–acetylated α–linked acidic dipeptidase (NAALA dipeptidase)," *J. Med. Chem,* (1990) 33, 2734–2744.

Coyle, J. et al., "N–acetyl–aspartyl glutamate," *Excitatory Amino Acids,* (1991) 69–77.

Tsai, G. et al., "Reductions in acidic amino acids and N–acetylaspartylglutamate in amyotrophic lateral sclerosis," *Brain Research,* (1991) 556, 151–156.

Tsai, G. et al., "Changes of excitatory neurotransmitter metabolism in schizophrenic brains," *Salmon Lecturer of the New York Academy of Medicine* (Dec. 2–3, 1993).

Rothstein, J. et al., "Abnormal excitatory amino acid metabolism in amyotrophic lateral sclerosis," *Anals of Neurology,* (1990) 28:1, 18–25.

Tsai, G. et al., "Immunocytochemical distribution of N–acetylaspartylglutamate in the rat forebrain and glutamatergic pathways," *J. of Chem. Neuroanatomy,* (1993) 6, 277–292.

Koenig, M. et al., "N–acetyl–aspartyl–glutamate (NNAG) elicits rapid increase in intraneuronal $Ca^{2+}$ in vitro," *NeuroReports,* (1994) 5, 1063–1068.

Woods, D. et al., "Gender–linked injury after focal ischemia," *Soc. for Neuroscience 1996 Abstract Form,* (1996).

Myerhoff, J. et al., "Genetically epilepsy–prone rats have increased brain regional activity of an enzyme which liberates glutamate from N–acetyl–aspartyl–glutamate," *Brain Research,* (1992) 593, 140–143.

Anderson, Vernon E. and W.W. Cleland. 1990. Biochemistry. 29: 10498–10503.

Blackburn, G. Michael and Abdul Rashid. 1988. J. Chem. Soc. Chem. Commun. (4): 317–319.

McFadden, Helen G. et al. 1987. Aust. J. Chem. 40:1619–1629.

Grobelny, Damian et al. 1985. Biochem. J. 232: 15–19.

Pfeiffer, Francis R. et al. 1974. J. Med. Chem. 17(1): 112–115.

Grobelny, Damian et al. Database CAPLUS on STN® International. 1990. Accession No. 1990:94404. [Biochemistry. 28(12): 4948–4951 (1990)].

PHOSPHONIC ACID DERIVATIVES

BACKGROUND OF THE INVENTION

1. Field of the Invention

The present invention relates to phosphonic acid derivatives that inhibit N-Acetylated α-Linked Acidic Dipeptidase (NAALADase) enzyme activity, pharmaceutical compositions comprising such derivatives, and methods of using such derivatives to inhibit NAALADase activity, to treat a glutamate abnormality and to treat a prostate disease in an animal.

2. Description of the Prior Art

Glutamate Abnormalities

Glutamate has been implicated in various neurological diseases and conditions, including epilepsy, stroke, Alzheimer's disease, Parkinson's Disease, Amyotrophic Lateral Sclerosis (ALS), Huntington's Disease, schizophrenia, chronic pain, ischemia and neuronal loss following hypoxia, hypoglycemia, ischemia, trauma and nervous insult. Neurons release glutamate in great quantities when they are deprived of oxygen, as may occur during an ischemic brain insult such as a stroke or a heart attack. This excess release of glutamate in turn causes over-stimulation (excitotoxicity) of NMDA, AMPA, Kainate and MGR receptors. When glutamate binds to these receptors, ion channels in the cell membranes of the neurons open, permitting flows of ions across the cell membranes, e.g., $Ca^{2+}$ and $Na^+$ into the cells and $K^+$ out of the cells. These flows of ions, especially the influx of $Ca^{2+}$, cause over-stimulation of the neurons. The over-stimulated neurons secrete more glutamate, creating a domino-effect which ultimately results in cell death via the production of proteases, lipases and free radicals.

Attempts to prevent excitotoxicity by blocking NMDA, AMPA, Kainate and MGR receptors have proven difficult because each receptor has multiple sites to which glutamate may bind. Many of the compositions that are effective in blocking the receptors are also toxic to animals. As such, there is currently no known effective treatment for glutamate abnormalities.

Prostate Cancer

Prostate cancer is the leading form of cancer and the second leading cause of death from cancer for men in the United States. The American Cancer Society has estimated that in 1996 alone, 317,100 new cases of prostate cancer were diagnosed and 41,400 deaths were caused by prostate cancer. The incidence rate of prostate cancer increased 65% between 1980 and 1990, and will continue to rise with improved screening tests and longer life expectancies. While most men used to die of other illnesses before prostate cancer had a chance to develop, higher prostate cancer mortality rates are expected as men live longer and the disease has more time to progress.

In 1993, the molecular cloning of Prostate Specific Membrane Antigen (PSMA) was reported as a potential prostate carcinoma marker and hypothesized to serve as a target for imaging and cytotoxic treatment modalities for prostate cancer. PSMA antibodies, particularly indium-111 labelled and itrium labelled PSMA antibodies, have been described and examined clinically for the diagnosis and treatment of prostate cancer. PSMA is expressed in prostatic ductal epithelium and is present in seminal plasma, prostatic fluid and urine. In 1996, it was found that the expression of PSMA cDNA confers the activity of NAALADase.

NAALADase Inhibitors

NAAG and NAALADase have been implicated in several human and animal pathological conditions. For example, it has been demonstrated that intra-hippocampal injections of NAAG elicit prolonged seizure activity. More recently, it was reported that rats genetically prone to epileptic seizures have a persistent increase in their basal level of NAALADase activity. These observations support the hypothesis that increased availability of synaptic glutamate elevates seizure susceptibility, and suggest that NAALADase inhibitors may provide anti-epileptic activity.

NAAG and NAALADase have also been implicated in the pathogenesis of ALS and in the pathologically similar animal disease called Hereditary Canine Spinal Muscular Atrophy (HCSMA). It has been shown that concentrations of NAAG and its metabolites—NAA, glutamate and aspartate—are elevated two- to three-fold in the cerebrospinal fluid of ALS patients and HCSMA dogs. Additionally, NAALADase activity is significantly increased (two- to three-fold) in post-mortem spinal cord tissue from ALS patients and HCSMA dogs. As such, NAALADase inhibitors may be clinically useful in curbing the progression of ALS if increased metabolism of NAAG is responsible for the alterations of CSF levels of these acidic amino acids and peptides.

Abnormalities in NAAG levels and NAALADase activity have also been documented in post-mortem schizophrenic brain, specifically in the prefrontal and limbic brain regions.

The findings described above suggest that NAALADase inhibitors could be useful in treating glutamate abnormalities. In fact, the results of studies conducted by the present inventors confirm that NAALADase inhibitors are not only effective in treating glutamate abnormalities, but also effective in treating prostate diseases, particularly prostate cancer. Although the cancer data relate to prostate cancer cells, NAALADase inhibitors are expected to be equally effective in treating cancer of other tissues where NAALADase enzyme reside, such as the brain, kidney and testis.

While a few NAALADase inhibitors have been identified, they have only been used in non-clinical research. Examples of such inhibitors include general metallopeptidase inhibitors such as o-phenanthroline, metal chelators such as EGTA and EDTA, and peptide analogs such as quisqualic acid and β-NAAG. Accordingly, a need exists for more NAALADase inhibitors to be identified and used in treatments of glutamate abnormalities and prostate diseases.

SUMMARY OF THE INVENTION

The present invention relates to phosphonic acid derivatives that inhibit NAALADase enzyme activity, pharmaceutical compositions comprising such derivatives, and methods of using such derivatives to inhibit NAALADase activity, to treat a glutamate abnormality and to treat a prostate disease in an animal.

Specifically, the present invention relates to a compound of formula I:

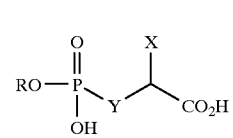

or a pharmaceutically acceptable salt or hydrate thereof, wherein:

Y is selected from the group consisting of $CR_1R_2$, $NR_3$ and O;

X is selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl and Ar, wherein said X is unsubstituted or substituted with carboxy, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino, Ar or mixtures thereof;

R, $R_1$, $R_2$ and $R_3$ are independently selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl and Ar, wherein said R, $R_1$, $R_2$ and $R_3$ are independently unsubstituted or substituted with $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino, Ar or mixtures thereof, provided that R is not hydrogen when X is hydrogen, carboxymethyl or carboxyethyl; and Ar is selected from the group consisting of 1-naphthyl, 2-naphthyl, 2-indolyl, 3-indolyl, 2-furyl, 3-furyl, 2-thienyl, 3-thienyl, 2-pyridyl, 3-pyridyl, 4-pyridyl, benzyl and phenyl, wherein said Ar has one to three substituent(s) independently selected from the group consisting of hydrogen, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino and mixtures thereof.

The present invention also relates to a pharmaceutical composition comprising:

(i) a therapeutically effective amount of the compound of formula I

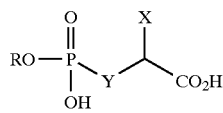

or a pharmaceutically acceptable salt or hydrate thereof, wherein:

Y is selected from the group consisting of $CR_1R_2$, $NR_3$ and O;

X is selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl and Ar, wherein said X is unsubstituted or substituted with carboxy, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino, Ar or mixtures thereof;

R, $R_1$, $R_2$ and $R_3$ are independently selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl and Ar, wherein said R, $R_1$, $R_2$ and $R_3$ are independently unsubstituted or substituted with $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino, Ar or mixtures thereof, provided that R is not hydrogen when X is carboxymethyl or carboxyethyl; and Ar is selected from the group consisting of 1-naphthyl, 2-naphthyl, 2-indolyl, 3-indolyl, 2-furyl, 3-furyl, 2-thienyl, 3-thienyl, 2-pyridyl, 3-pyridyl, 4-pyridyl, benzyl and phenyl, wherein said Ar has one to three substituent(s) independently selected from the group consisting of hydrogen, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino and mixtures thereof; and (ii) a pharmaceutically acceptable carrier.

The present invention further relates to a method of inhibiting NAALADase enzyme activity in an animal, comprising administering an effective amount of the compound of formula I to said animal.

Additionally, the present invention relates to method of treating a glutamate abnormality in an animal, comprising administering an effective amount of the compound of formula I to said animal.

Finally, the present invention relates to a method of treating a prostate disease in an animal, comprising administering an effective amount of the compound of formula I to said animal.

DETAILED DESCRIPTION OF THE INVENTION

Definitions

Figure 1:
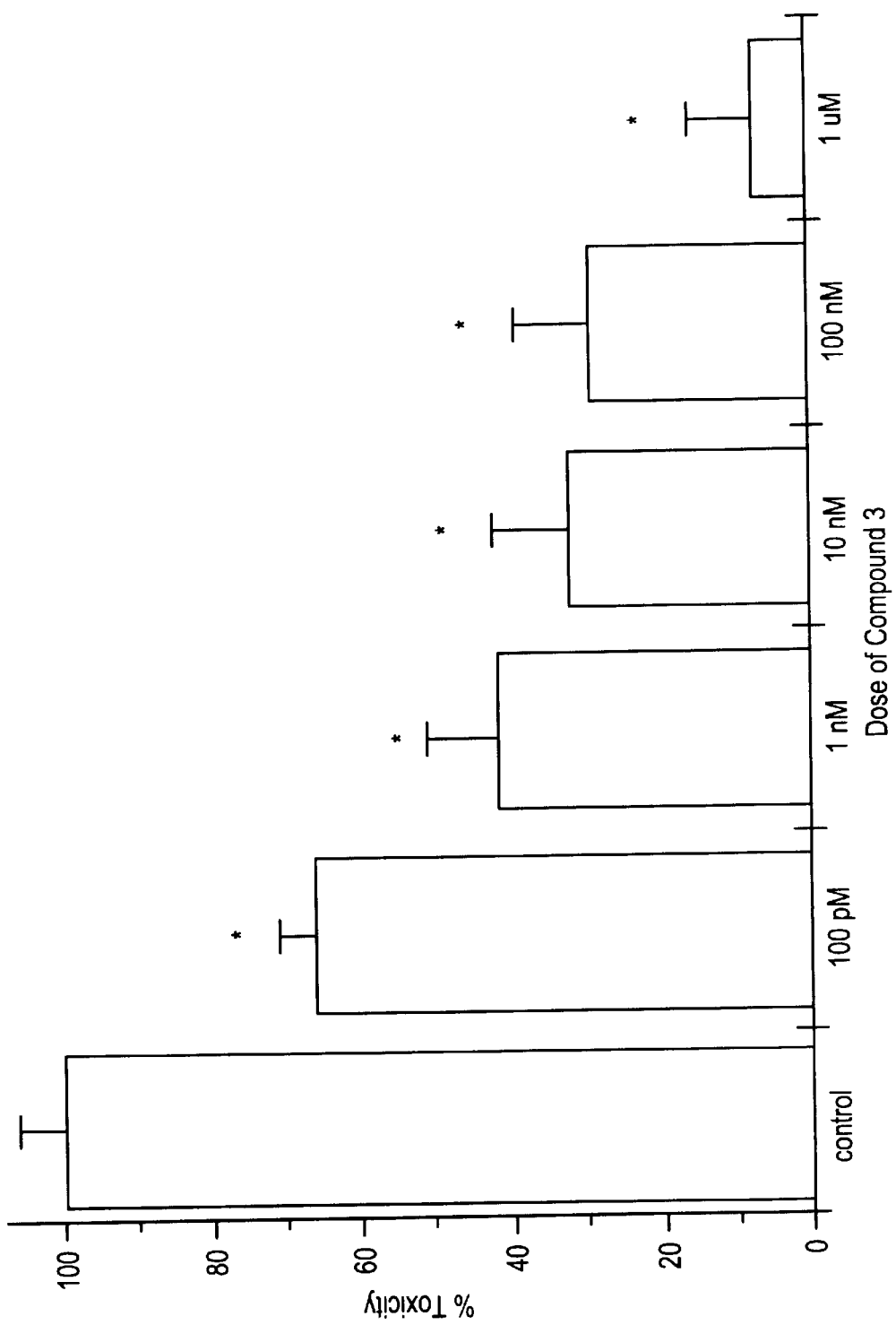
FIG. 1 is a bar graph plotting in vitro toxicity of ischemic insult (potassium cyanide and 2-deoxyglucose) against various doses of 2-(phosphonomethyl)pentanedioic acid with which cortical cell cultures were treated.

"Compound 3" refers to 2-(phosphonomethyl) pentanedioic acid, a NAALADase inhibitor. "Glutamate abnormality" refers to any disease, disorder or condition in which glutamate is implicated, and includes without limitation epilepsy, stroke, Alzheimer's disease, Parkinson's Disease, Amyotrophic Lateral Sclerosis (ALS), Huntington's Disease, schizophrenia, chronic pain, ischemia and neuronal insult.

"Glutamate modulator" refers to any composition of matter which alone or in combination with another agent affects the level of glutamate in an animal.

"Inhibition", in the context of enzymes, refers to reversible enzyme inhibition such as competitive, uncompetitive and non-competitive inhibition. Competitive, uncompetitive and non-competitive inhibition can be distinguished by the effects of an inhibitor on the reaction kinetics of an enzyme. Competitive inhibition occurs when the inhibitor combines reversibly with the enzyme in such a way that it competes with a normal substrate for binding at the active site. The affinity between the inhibitor and the enzyme may be measured by the inhibitor constant, $K_i$, which is defined as:

$$K_i = \frac{[E][I]}{[EI]}$$

wherein [E] is the concentration of the enzyme, [I] is the concentration of the inhibitor, and [EI] is the concentration of the enzyme-inhibitor complex formed by the reaction of the enzyme with the inhibitor. Unless otherwise specified, $K_i$ as used herein refers to the affinity between the inventive compounds and NAALADase. "IC50" is a related term used to define the concentration or amount of a compound which is required to cause a 50% inhibition of the target enzyme.

"Ischemia" refers to localized tissue anemia due to obstruction of the inflow of arterial blood. Global ischemia occurs when blood flow to the entire brain ceases for a period of time, such as may result from cardiac arrest. Focal ischemia occurs when a portion of the brain is deprived of its normal blood supply, such as may result from thromboembolytic occlusion of a cerebral vessel, traumatic head injury, edema or brain tumor. Even if transient, both global and focal ischemia can produce widespread neuronal damage. Although nerve tissue damage occurs over hours or even days following the onset of ischemia, some permanent nerve tissue damage may develop in the initial minutes following cessation of blood flow to the brain. Much of this damage is attributed to glutamate toxicity and secondary consequences of reperfusion of the tissue, such as the release of vasoactive products by damaged endothelium, and the release of cytotoxic products, such as free radicals and leukotrienes, by the damaged tissue.

"NAAG" refers to N-acetyl-aspartyl-glutamate, an important peptide component of the brain, with levels comparable to the major inhibitor neurotransmitter gamma-aminobutyric acid (GABA) NAAG is neuron-specific, present in synaptic vesicles and released upon neuronal stimulation in several systems presumed to be glutamatergic. Studies suggest that NAAG may function as a neurotransmitter and/or neuromodulator in the central nervous system, or as a precursor of the neurotransmitter glutamate.

"NAALADase" refers to N-acetylated α-linked acidic dipeptidase, a membrane-bound metallopeptidase which catabolizes NAAG to N-acetylaspartate (NAA) and glutamate:

Catabolism of NAAG by NAALADase

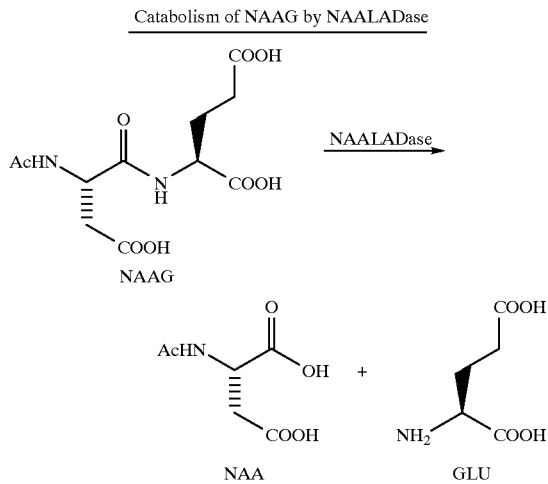

NAALDase shows a high affinity for NAAG with a Km of 540 nM. If NAAG is a bioactive peptide, then NAALADase may serve to inactivate NAAG'S synaptic action. Alternatively, if NAAG functions as a precursor for glutamate, the primary function of NAALADase may be to regulate synaptic glutamate availability.

"Nervous function" refers to the various functions of the nervous system, which among other things provide an awareness of the internal and external environments of the body, make possible voluntary and reflex activities between the various structural elements of the organism, and balance the organism's response to environmental changes.

"Nervous insult" refers to any damage to nervous tissue and any disability or death resulting therefrom. The cause of nervous insult may be metabolic, toxic, neurotoxic, iatrogenic, thermal or chemical, and includes without limitation ischemia, hypoxia, cerebrovascular accident, trauma, surgery, pressure, mass effect, hemorrhage, radiation, vasospasm, neurodegenerative disease, neurodegenerative process, infection, Parkinson's disease, ALS, myelination/demyelination process, epilepsy, cognitive disorder, glutamate abnormality and secondary effects thereof. Currently, there is no known effective treatment for nervous tissue damage.

"Nervous tissue" refers to the various components that make up the nervous system, including without limitation neurons, neural support cells, glia, Schwann cells, vasculature contained within and supplying these structures, the central nervous system, the brain, the brain stem, the spinal cord, the junction of the central nervous system with the peripheral nervous system, the peripheral nervous system and allied structures.

"Neuroprotective" refers to the effect of reducing, arresting or ameliorating nervous insult, and protecting, resuscitating or reviving nervous tissue which has suffered nervous insult.

"Pharmaceutically acceptable salt" refers to a salt of the inventive compounds which possesses the desired pharmacological activity and which is neither biologically nor otherwise undesirable. The salt can be formed with inorganic acids such as acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate heptanoate, hexanoate, hydrochloride hydrobromide, hydroiodide, 2-hydroxyethanesulfonate, lactate, maleate, methanesulfonate, 2-naphthalenesulfonate, nicotinate, oxalate, thiocyanate, tosylate and undecanoate. Examples of a base salt include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine. The basic nitrogen-containing groups can be quarternized with agents including lower alkyl halides such as methyl, ethyl, propyl and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as benzyl and phenethyl bromides.

"Prostate disease" refers to any disease, disorder or condition of the prostate, including prostate cancer, such as adenocarcinoma or metastatic cancers, and conditions characterized by abnormal growth of prostatic epithelial cells, such as benign prostatic hyperplasia.

"PSA" refers to Prostate Specific Antigen, a well known prostate cancer marker. It is a protein produced by prostate cells and is frequently present at elevated levels in the blood of men with prostate cancer. PSA correlates with tumor burden, serves as an indicator of metastatic involvement, and provides a parameter for following a prostate cancer patient's response to surgery, irradiation and androgen replacement therapy.

"PSMA" refers to Prostate Specific Membrane Antigen, a potential prostate carcinoma marker that has been hypothesized to serve as a target for imaging and cytotoxic treatment modalities for prostate cancer. PSMA is expressed in prostatic ductal epithelium and is present in seminal plasma, prostatic fluid and urine. It has been found that the expression of PSMA cDNA confers the activity of NAALADase.

"Treatment" refers to:

(i) preventing a disease, disorder or condition from occurring in an animal which may be predisposed to the disease, disorder and/or condition but has not yet been diagnosed as having it;

(ii) inhibiting the disease, disorder or condition, i.e., arresting its development; and (iii) relieving the disease, disorder or condition, i.e., causing regression of the disease, disorder and/or condition.

Compound of the Present Invention

The present invention relates to a compound of formula I:

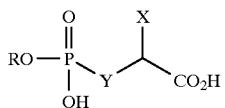

or a pharmaceutically acceptable salt or hydrate thereof, wherein:

Y is selected from the group consisting of $CR_1R_2$, $NR_3$ and O;

X is selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl and Ar, wherein said X is unsubstituted or substituted with carboxy, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino, Ar or mixtures thereof; R, $R_1$, $R_2$ and $R_3$ are independently selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl and Ar, wherein said R, $R_1$, $R_2$ and $R_3$ are independently unsubstituted or substituted with $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino, Ar or mixtures thereof, provided that R is not hydrogen when X is hydrogen, carboxymethyl or carboxyethyl; and Ar is selected from the group consisting of 1-naphthyl, 2-naphthyl, 2-indolyl, 3-indolyl, 2-furyl, 3-furyl, 2-thienyl, 3-thienyl, 2-pyridyl, 3-pyridyl, 4-pyridyl, benzyl and phenyl, wherein said Ar has one to three substituent(s) independently selected from the group consisting of hydrogen, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino and mixtures thereof.

In a preferred embodiment, Y is $CH_2$.

In a more preferred embodiment, R is hydrogen or X is substituted with carboxy.

In an even more preferred embodiment, X is carboxyethyl.

In the most preferred embodiment, the compound is selected from the group consisting of:
2-methyl-3-phosphonopropanoic acid;
2-ethyl-3-phosphonopropanoic acid;
2-propyl-3-phosphonopropanoic acid;
2-butyl-3-phosphonopropanoic acid;
2-phenyl-3-phosphonopropanoic acid;
2-(2-phenylethyl)-3-phosphonopropanoic acid;
2-(3-phenylpropyl)-3-phosphonopropanoic acid;
2-(4-pyridyl)-3-phosphonopropanoic acid;
2-benzyl-3-phosphonopropanoic acid;
2-O-(methylphosphonomethyl)pentanedioic acid;
2-O-(ethylphosphonomethyl)pentanedioic acid;
2-O-(propylphosphonomethyl)pentanedioic acid;
2-O-(butylphosphonomethyl)pentanedioic acid;
2-O-(phenylphosphonomethyl)pentanedioic acid;
2-O-[(2-phenylethyl)phosphonomethyl]pentanedioic acid;
2-O-[(3-phenylpropyl)phosphonomethyl]pentanedioic acid;
2-O-[(4-pyridyl)phosphonomethyl]pentanedioic acid; and
2-O-(benzylphosphonomethyl)pentanedioic acid.

Synthesis of Compounds

The compounds of the present invention can be readily prepared by standard techniques of organic chemistry, utilizing the general synthetic pathways depicted below (see Schemes I, II and III). Precursor compounds may be prepared by methods known in the art.

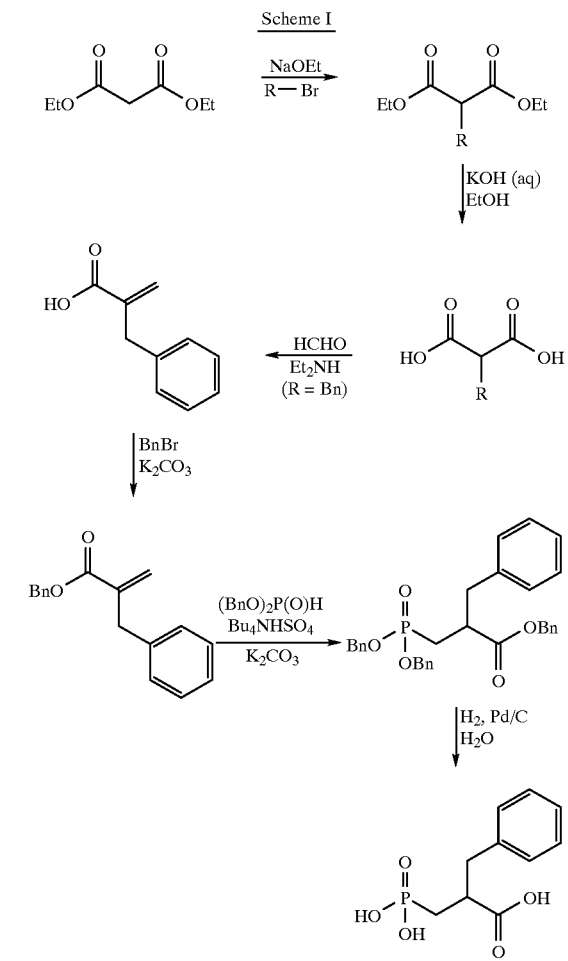

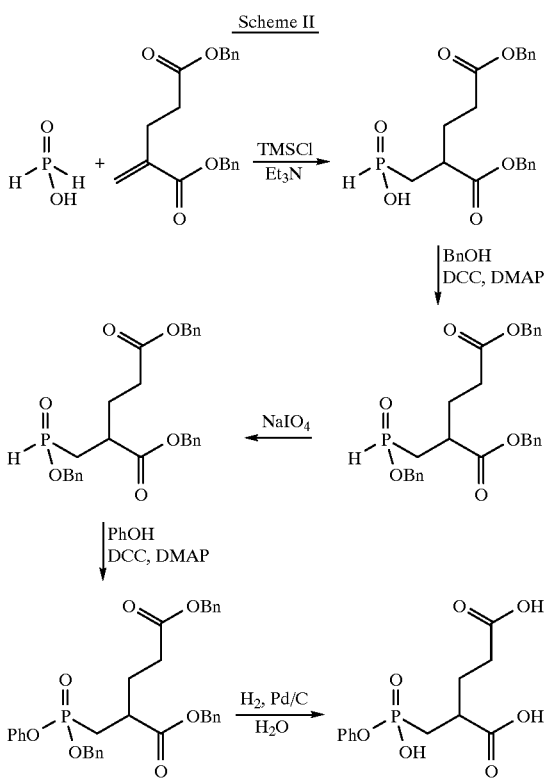

Scheme II

Pharmaceutical Compositions of the Present Invention

The present invention also relates to a pharmaceutical composition comprising:
(i) a therapeutically effective amount of the compound of formula I

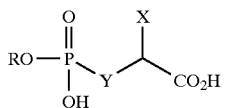

I or a pharmaceutically acceptable salt or hydrate thereof, wherein:

Y is selected from the group consisting of $CR_1R_2$, $NR_3$ and O;

X is selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl and Ar, wherein said X is unsubstituted or substituted with carboxy, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino, Ar or mixtures thereof;

R, $R_1$, $R_2$ and $R_3$ are independently selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl and Ar, wherein said R, $R_1$, $R_2$ and $R_3$ are independently unsubstituted or substituted with $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino, Ar or mixtures thereof, provided that R is not hydrogen when X is carboxymethyl or carboxyethyl; and Ar is selected from the group consisting of 1-naphthyl, 2-naphthyl, 2-indolyl, 3-indolyl, 2-furyl, 3-furyl, 2-thienyl, 3-thienyl, 2-pyridyl, 3-pyridyl, 4-pyridyl, benzyl and phenyl, wherein said Ar has one to three substituent(s) independently selected from the group consisting of hydrogen, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino and mixtures thereof; and (ii) a pharmaceutically acceptable carrier.

Preferably, in said compound, Y is $CH_2$.

More preferably, R is hydrogen or X is substituted with carboxy.

Even more preferably, X is carboxyethyl.

Most preferably, the compound is selected from the group consisting of:
phosphonopropanoic acid;
2-methyl-3-phosphonopropanoic acid;
2-ethyl-3-phosphonopropanoic acid;
2-propyl-3-phosphonopropanoic acid;
2-butyl-3-phosphonopropanoic acid;
2-phenyl-3-phosphonopropanoic acid;
2-(2-phenylethyl)-3-phosphonopropanoic acid;
2-(3-phenylpropyl)-3-phosphonopropanoic acid;
2-(4-pyridyl)-3-phosphonopropanoic acid;
2-benzyl-3-phosphonopropanoic acid;
2-O-(methylphosphonomethyl)pentanedioic acid;
2-O-(ethylphosphonomethyl)pentanedioic acid;
2-O-(propylphosphonomethyl)pentanedioic acid;
2-O-(butylphosphonomethyl)pentanedioic acid;
2-O-(phenylphosphonomethyl)pentanedioic acid;
2-O-[(2-phenylethyl)phosphonomethyl]pentanedioic acid;
2-O-[(3-phenylpropyl)phosphonomethyl]pentanedioic acid;
2-O-[(4-pyridyl)phosphonomethyl]pentanedioic acid; and
2-O-(benzylphosphonomethyl)pentanedioic acid.

In another preferred embodiment, the pharmaceutical composition further comprises a therapeutic agent selected from the group consisting of therapeutic hormones, chemotherapeutic agents, monoclonal antibodies, anti-angiogenesis agents, radiolabelled compounds, antineoplastic agents and mixtures thereof. Examples of therapeutic hormones include diethylstilbestrol (DES), leuprolide, flutamide, cyproterone acetate, ketoconazole and amino glutethimide are preferred. Examples of antineoplastic agents include 5-fluorouracil, vinblastine sulfate, estramustine phosphate, suramin and strontium-89. Examples of chemotherapeutic agents include buserelin, chlorotranisene, chromic phosphate, cisplatin, cyclophosphamide, dexamethasone, doxorubicin, estradiol, estradiol valerate, estrogens conjugated and esterified, estrone, ethinyl estradiol, floxuridine, goserelin, hydroxyurea, melphalan, methotrexate, mitomycin and prednisone.

In a further preferred embodiment, the compound of formula I is present in an amount that is effective for inhibiting NAALADase activity in an animal, treating a glutamate abnormality in an animal or treating a prostate disease in an animal.

Methods of Use of the Present Invention

Method of Inhibiting Naaladase Enzyme Activity

The present invention further relates to a method of inhibiting NAALADase enzyme activity in an animal, comprising administering an effective amount of the compound of formula I to said animal.

Method of Treating a Glutamate Abnormality

Although not limited to any one particular theory, it is believed that the compounds of the present invention modulate levels of glutamate by acting on a storage form of glutamate which is hypothesized to be upstream from the effects mediated by the NMDA receptor.

Accordingly, the present invention additionally relates to a method of treating a glutamate abnormality in an animal, comprising administering an effective amount of the compound of formula I to said animal.

In a preferred embodiment, said glutamate abnormality is selected from the group consisting of epilepsy, stroke, Alzheimer's disease, Parkinson's Disease, Amyotrophic Lateral Sclerosis (ALS), Huntington's Disease, disease, schizophrenia, chronic pain, ischemia and neuronal insult.

In a more preferred embodiment, said glutamate abnormality is ischemia.

Method of Treating Prostate Disease

The present invention also relates to a method of treating a prostate disease in an animal, comprising administering an effective amount of the compound of formula I to said animal.

In a preferred embodiment, said prostate disease is prostate cancer or benign prostatic hyperplasia.

Method of Treating Cancer

In addition to prostate cancer, other forms of cancer that may be treated with the compounds of the present invention include without limitation: ACTH-producing tumors, acute lymphocytic leukemia, acute nonlymphocytic leukemia, cancer of the adrenal cortex, bladder cancer, brain cancer, breast cancer, cervix cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head & neck cancer, Hodgkin's lymphoma, Kaposi's sarcoma, kidney cancer, liver cancer, lung cancer (small and/or non-small cell), malignant peritoneal effusion, malignant pleural effusion, melanoma, mesothelioma, multiple myeloma, neuroblastoma, non-Hodgkin's lymphoma, osteosarcoma, ovary cancer, ovary (germ cell) cancer, pancreatic cancer, penis cancer, retinoblastoma, skin cancer, soft-tissue sarcoma, squamous cell carcinomas, stomach cancer, testicular cancer, thyroid cancer, trophoblastic neoplasms, cancer of the uterus, vaginal cancer, cancer of the vulva and Wilm's tumor.

The compounds of the present invention are particularly useful in treating cancer of tissues where NAALADase enzymes reside. Such tissues include the prostate as well as the brain, kidney and testis.

Route of Administration

In the methods of the present invention, the compounds may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term parenteral as used herein includes subcutaneous, intravenous, intramuscular, intraperitoneal, intrathecal, intraventricular, intrasternal or intracranial injection and infusion techniques. Invasive techniques are preferred, particularly direct administration to damaged neuronal tissue.

To be effective therapeutically as central nervous system targets, the compounds of the present invention should readily penetrate the blood-brain barrier when peripherally administered. Compounds which cannot penetrate the blood-brain barrier can be effectively administered by an intraventricular route.

The compounds may also be administered in the form of sterile injectable preparations, for example, as sterile injectable aqueous or oleaginous suspensions. These suspensions can be formulated according to techniques known in the art using suitable dispersing or wetting agents and suspending agents. The sterile injectable preparations may also be sterile injectable solutions or suspensions in non-toxic parenterally-acceptable diluents or solvents, for example, as solutions in 1,3-butanediol. Among the acceptable vehicles and solvents that may be employed are water, Ringer's solution and isotonic sodium chloride solution. In addition, sterile fixed oils are conventionally employed as solvents or suspending mediums For this purpose, any bland fixed oil such as a synthetic mono- or di-glyceride may be employed. Fatty acids such as oleic acid and its glyceride derivatives, including olive oil and castor oil, especially in their polyoxyethylated forms, are useful in the preparation of injectables. These oil solutions or suspensions may also contain long-chain alcohol diluents or dispersants.

Additionally, the compounds may be administered orally in the form of capsules, tablets, aqueous suspensions or solutions. Tablets may contain carriers such as lactose and corn starch, and/or lubricating agents such as magnesium stearate. Capsules may contain diluents including lactose and dried corn starch. Aqueous suspensions may contain emulsifying and suspending agents combined with the active ingredient. The oral dosage forms may further contain sweetening and/or flavoring and/or coloring agents.

The compounds may further be administered rectally in the form of suppositories. These compositions can be prepared by mixing the drug with suitable non-irritating excipients which are solid at room temperature, but liquid at rectal temperature such that they will melt in the rectum to release the drug. Such excipients include cocoa butter, beeswax and polyethylene glycols.

Moreover, the compounds may be administered topically, especially when the conditions addressed for treatment involve areas or organs readily accessible by topical application, including neurological disorders of the eye, the skin or the lower intestinal tract.

For topical application to the eye, or ophthalmic use, the compounds can be formulated as micronized suspensions in isotonic, pH adjusted sterile saline or, preferably, as a solution in isotonic, pH adjusted sterile saline, either with or without a preservative such as benzylalkonium chloride. Alternatively, the compounds may be formulated into ointments, such as petrolatum.

For topical application to the skin, the compounds can be formulated into suitable ointments containing the compounds suspended or dissolved in, for example, mixtures with one or more of the following: mineral oil, liquid petrolatum, white petrolatum, propylene glycol, polyoxyethylene polyoxypropylene compound, emulsifying wax and water. Alternatively, the compounds can be formulated into suitable lotions or creams containing the active compound suspended or dissolved in, for example, a mixture of one or more of the following: mineral oil, sorbitan monostearate, polysorbate 60, cetyl ester wax, cetearyl alcohol, 2-octyldodecanol, benzyl alcohol and water.

Topical application to the lower intestinal tract can be effected in rectal suppository formulations (see above) or in suitable enema formulations.

The compounds of the present invention may be administered by a single dose, multiple discrete doses or continuous infusion. Since the compounds are small, easily diffusible and relatively stable, they are well suited to continuous infusion. Pump means, particularly subcutaneous pump means, are preferred for continuous infusion.

Dosage

Dose levels on the order of about 0.1 mg to about 10,000 mg of the active ingredient compound are useful in the treatment of the above conditions, with preferred levels being about 0.1 mg to about 1,000 mg. The specific dose level for any particular patient will vary depending upon a variety of factors, including the activity of the specific compound employed; the age, body weight, general health, sex and diet of the patient; the time of administration; the rate of excretion; drug combination; the severity of the particular disease being treated; and the form of administration. Typically, in vitro dosage-effect results provide useful guidance on the proper doses for patient administration. Studies in animal models are also helpful, particularly in determining effective doses for treating cancer. The considerations for determining the proper dose levels are well known in the art.

In a preferred embodiment, the compounds of the present invention are administered in lyophilized form. In this case, 1 to 100 mg of a compound of the present invention may be lyophilized in individual vials, together with a carrier and a buffer, such as mannitol and sodium phosphate. The compound may be reconstituted in the vials with bacteriostatic water before administration.

In treating global ischemia, the compounds of the present invention are preferably administered orally, rectally, parenterally or topically at least 1 to 6 times daily, and may follow an initial bolus dose of higher concentration.

As previously mentioned, the compounds of the present invention may be administered in combination with one or more therapeutic agents, including chemotherapeutic agents. TABLE I provides known median dosages for selected chemotherapeutic agents. Specific dose levels for these agents will depend upon considerations such as those identified above for the compounds of the present invention.

TABLE I

| CHEMOTHERAPEUTIC AGENT | MEDIAN DOSAGE |
|---|---|
| Asparaginase | 10,000 units |
| Bleomycin Sulfate | 15 units |
| Carboplatin | 50–450 mg |
| Carmustine | 100 mg |
| Cisplatin | 10–50 mg |
| Cladribine | 10 mg |
| Cyclophosphamide (lyophilized) | 100 mg–2 gm |
| Cyclophosphamide (non-lyophilized) | 100 mg–2 gm |
| Cytarabine (lyophilized powder) | 100 mg–2 gm |
| Dacarbazine | 100 mg–200 mg |
| Dactinomycin | 0.5 mg |
| Daunorubicin | 20 mg |
| Diethylstilbestrol | 250 mg |
| Doxorubicin | 10–150 mg |
| Etidronate | 300 mg |
| Etoposide | 100 mg |
| Floxuridine | 500 mg |
| Fludarabine Phosphate | 50 mg |
| Fluorouracil | 500 mg–5 gm |
| Goserelin | 3.6 mg |
| Granisetron Hydrochloride | 1 mg |
| Idarubicin | 5–10 mg |
| Ifosfamide | 1–3 gm |
| Leucovorin Calcium | 50–350 mg |
| Leuprolide | 3.75–7.5 mg |
| Mechlorethamine | 10 mg |
| Medroxyprogesterone | 1 gm |
| Melphalan | 50 gm |
| Methotrexate | 20 mg–1 gm |
| Mitomycin | 5–40 mg |
| Mitoxantrone | 20–30 mg |
| Ondansetron Hydrochloride | 40 mg |
| Paclitaxel | 30 mg |
| Pamidronate Disodium | 30–*90 mg |
| Pegaspargase | 750 units |

TABLE I-continued

| CHEMOTHERAPEUTIC AGENT | MEDIAN DOSAGE |
|---|---|
| Plicamycin | 2,500 mcgm |
| Streptozocin | 1 gm |
| Thiotepa | 15 mg |
| Teniposide | 50 mg |
| Vinblastine | 10 mg |
| Vincristine | 1–5 mg |
| Aldesleukin | 22 million units |
| Epoetin Alfa | 2,000–10,000 units |
| Filgrastim | 300–480 mcgm |
| Immune Globulin | 500 mg–10 gm |
| Interferon Alpha-2a | 3–36 million units |
| Interferon Alpha-2b | 3–50 million units |
| Levamisole | 50 mg |
| Octreotide | 1,000–5,000 mcgm |
| Sargramostim | 250–500 mcgm |

Administration Regimen

For the methods of the present invention, any administration regimen regulating the timing and sequence of drug delivery can be used and repeated as necessary to effect treatment. Such regimen may include pretreatment and/or co-administration with additional therapeutic agents.

a. Administration for Nervous Insult

To maximize protection of nervous tissue from nervous insult, the compounds of the present invention should be administered to the affected cells as soon as possible. In situations where nervous insult is anticipated, the compounds should be administered before the expected nervous insult. Such situations of increased likelihood of nervous insult include surgery (cartoid endarterectomy, cardiac, vascular, aortic, orthopedic); endovascular procedures such as arterial catherization (cartoid, vertebral, aortic, cardia, renal, spinal, Adamkiewicz); injections of embolic agents; coils or balloons for hemostasis; interruptions of vascularity for treatment of brain lesions; and predisposing medical conditions such as crescendo transient ischemic attacks, emboli and sequential strokes. Where pretreatment for stroke or ischemia is impossible or impracticable, it is important to get the compounds of the present invention to the affected cells as soon as possible during or after the event. In the time period between strokes, diagnosis and treatment procedures should be minimized to save the cells from further damage and death.

b. Administration for Prostate Disease

For patients with prostate cancer that is neither advanced nor metastatic, the compounds of the present invention may be administered (i) prior to surgery or radiation treatment to reduce the risk of metastasis; (ii) during surgery or in conjunction with radiation treatment; and/or (iii) after surgery or radiation therapy to reduce the risk of recurrence and to inhibit the growth of any residual tumorous cells.

For patients with advanced or metastatic prostate cancer, the compounds of the present invention may be administered as a continuous supplement to, or as a replacement for, hormonal ablation in order to slow tumor cell growth in both the untreated primary tumor and the existing metastatic lesions.

The methods of the present invention are particularly useful where shed cells could not be removed by surgical intervention. After post-surgical recovery, the methods of the present invention would be effective in reducing the chances of recurrence of a tumor engendered by such shed cells.

Combination with other Treatment a. Nervous Insult

In methods of treating nervous insult (particularly acute ischemic stroke and global ischemia caused by drowning and head trauma), the compounds of the present invention can be co-administered with one or more therapeutic agents, preferably agents which can reduce the risk of stroke (such as aspirin), and more preferably agents which can reduce the risk of a second ischemic event (such as ticlopidine).

The compounds of the present invention can be co-administered with one or more therapeutic agents either (i) together in a single formulation, or (ii) separately in individual formulations designed for optimal release rates of their respective active agent. Each formulation may contain from about 0.01% to about 99.99% by weight, preferably from about 3.5% to about 60% by weight, of a compound of the present invention, as well as one or more pharmaceutical excipients, such as wetting, emulsifying and pH buffering agents.

b. Prostate Disease (i) Surgery and Radiation Treatment

In general, surgery and radiation treatment are employed as potentially curative therapies for patients with localized prostate cancer who are under 70 years of age and are expected to live at least 10 more years.

Approximately 70% of newly diagnosed prostate cancer patients fall into this category. Approximately 90% of these patients (65% of total patients) undergo surgery, while approximately 10% of these patients (7% of total patients) undergo radiation treatment.

Histopathological examination of surgical specimens reveals that approximately 63% of patients undergoing surgery (40% of total patients) have locally extensive tumors or regional (lymph node) metastasis that was undetected at initial diagnosis. These patients are at a significantly greater risk of recurrence. Approximately 40% of these patients will actually develop recurrence within five years after surgery. Results after radiation treatment are even less encouraging. Approximately 80% of patients who have undergone radiation treatment as their primary therapy have disease persistence or develop recurrence or metastasis within five years after treatment.

Currently, most prostate cancer patients undergoing surgery and radiation treatment do not receive any immediate follow-up therapy. Rather, they are monitored frequently for elevated Prostate Specific Antigen ("PSA"), which is the primary indicator of recurrence or metastasis.

Based on the above statistics, there is considerable opportunity to use the present invention in conjunction with surgery and/or radiation treatment.

(ii) Hormonal Therapy

Hormonal ablation is the most effective palliative treatment for the 10% of patients with metastatic prostate cancer. Hormonal ablation by medication and/or orchiectomy is used to block hormones that promote further growth and metastasis of prostate cancer. With time, both the primary and metastatic tumors of virtually all of these patients become hormone-independent and resistant to therapy. Approximately 50% of patients with metastatic cancer die within three years after initial diagnosis, and 75% of such patients die within five years after diagnosis. Continuous supplementation with the compounds of the present invention may be used to prevent or reverse this potentially metastasis-permissive state.

(iii) Chemotherapy

While chemotherapy has been successful in treating some forms of cancer, it has shown slight therapeutic value in treating prostate cancer where it is generally reserved as a last resort. Accordingly, the opportunity to treat prostate cancer by combining chemotherapy with the methods of the present invention will be rare. When combined, however, such treatments should be more effective than chemotherapy alone in controlling prostate cancer.

(iv) Immunotherapy

The compounds of the present invention may also be used in combination with monoclonal antibodies to treat prostate cancer. Such combined treatment is particularly effective for patients with pelvic lymph node involvement, of which only 34% survive after 5 years. An example of such monoclonal antibodies is cell membrane-specific anti-prostate antibody.

The present invention may also be used with immunotherapies based on polyclonal or monoclonal antibody-derived reagents. Monoclonal antibody-derived reagents are preferred. These reagents are well known in the art, and include radiolabelled monoclonal antibodies such as monoclonal antibodies conjugated with strontium-89.

(v) Cryotherapy

The methods of the present invention may also be used in conjunction with cryotherapy for treatment of prostate cancer.

In Vitro Assay of NAALADase Activity

The following compounds of the present invention were tested for in vitro inhibition of NAALADase activity: 2-(2-phenylethyl)-3-phosphonopropanoic acid, 2-methyl-3-phosphonopropanoic acid, 2-benzyl-3-phosphonopropanoic acid and phosphonopropanoic acid. The results are provided in Table II below.

TABLE II

IN VITRO ACTIVITY

| Compound | $K_i$ |
|---|---|
| 2-(2-phenylethyl)-3-phosphonopropanoic acid | 199 nM |
| 2-methyl-3-phosphonopropanoic acid | 2.0 $\mu$M |
| 2-benzyl-3-phosphonopropanoic acid | 548 nM |

TABLE II-continued

IN VITRO ACTIVITY

| Compound | $K_i$ |
|---|---|
| 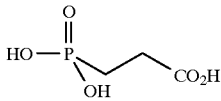 | 234 nM |

The results show that the compounds of the present invention are active in inhibiting NAALADase activity.

Protocol for In Vitro Assay of NAALADase Activity

The amount of [$^3$H]Glu liberated from [$^3$H]NAAG in 50 mM Tris-Cl buffer was measured for 15 minutes at 37° C. using 30–50 μg of synaptosomal protein. Substrate and product were resolved by anion-exchange liquid chromatography. Duplicate assays were performed so that no more than 20% of the NAAG was digested, representing the linear range of peptidase activity. Quisqualate (100 μM) was included in parallel assay tubes to confirm the specificity of the measurements.

Studies of Related Compounds

The following experimental studies of related compounds provide strong evidence that the compounds of the present invention are non-toxic and are effective in inhibiting NAALADase activity, treating glutamate abnormalities and treating prostate diseases.

In Vivo Toxicity of NAALADase Inhibitors

To examine the toxicological effect of NAALADase inhibition in vivo, a group of mice were injected with 2-(phosphonomethyl)pentanedioic acid, a NAALADase inhibitor of high activity, in doses of 1, 5, 10, 30, 100, 300 and 500 mg/kg body weight. The mice were subsequently observed two times per day for 5 consecutive days. The survival rate at each dose level is provided in TABLE III below. The results show that the NAALADase inhibitor is non-toxic to mice, suggesting that the compounds of the present invention would be similarly non-toxic to humans when administered at therapeutically effective amounts.

TABLE III

TOXICOLOGICAL EFFECTS OF NAALADASE INHIBITORS

| Dose (mg/kg) | 1 | 5 | 10 | 30 | 100 | 300 | 500 |
|---|---|---|---|---|---|---|---|
| Survival Rate After 5 days (%) | 100 | 100 | 100 | 100 | 100 | 100 | 66.7 |

In Vitro Assay of NAALADase Activity

The following three compounds were tested for in vitro inhibition of NAALADase activity: 2-(phosphonomethyl) pentanedioic acid, 2-(phosphonomethyl)succinic acid, and 2-[[2-carboxyethyl)hydroxyphosphinol]methyl] pentanedioicacid. The results are provided in Table IV below.

TABLE IV

IN VITRO ACTIVITY OF NAALADASE INHIBITORS

| Compound | $K_i$ (nM) |
|---|---|
| 2-(phosphonomethyl)pentanedioic acid | 0.275 ± 0.08 |
| 2-(phosphonomethyl)succinic acid | 700.00 ± 67.3 |
| 2-[[(2-carboxyethyl)hydroxyphosphinol]-methyl]pentanedioic acid) | 1.89 ± 0.19 |

The results show that 2-(phosphonomethyl)pentanedioic acid exhibits high NAALADase inhibiting activity, with a $K_i$ of 0.27 nM. The activity of this compound is over 1000 times greater than that of previously described NAALADase inhibitors. Since 2-(phosphonomethyl)pentanedioic acid is similar in structure to the compounds of the present invention, the results suggest that the compounds of the present invention would also be potent NAALADase inhibitors.

By comparison, 2-(phosphonomethyl)succinic acid exhibits much lower NAALADase inhibiting activity, suggesting that a glutamate analog attached to the phosphonic acid contributes to its NAALADase inhibiting activity.

The results also show that 2-[[2-carboxyethyl) hydroxyphosphinol]methyl]pentanedioic acid, which has an additional carboxylic acid side chain similar to the aspartate residue found in NAAG, exhibits a lower NAALADase inhibiting activity than 2-(phosphonomethyl)pentanedioic acid.

The protocol for the in vitro assay of NAALADase activity is the same as that described above regarding the compounds of the present invention.

In Vitro Assay of NAALADase Inhibitors on ischemia

To examine the effect of NAALADase inhibitors on in vitro ischemic toxicity, cortical cell cultures were treated with 2-(phosphonomethyl)pentanedioic acid (in concentrations ranging from 100 pM to 1 μM) during an ischemic insult and for one hour thereafter. The toxicity measurement for each concentration of the NAALADase inhibitor is provided in TABLE V below and graphically represented in FIG. 1.

TABLE V

| Dose | % Toxicity |
|---|---|
| Control | 100.00 ± 9.0 (n = 5) |
| 100 pM | 66.57 ± 4.38 (n = 5) |
| 1 nM | 42.31 ± 9.34 (n = 5) |
| 10 nM | 33.08 ± 9.62 (n = 5) |
| 100 nM | 30.23 ± 9.43 (n = 5) |
| 1 μM | 8.56 ± 8.22 (n = 5) |

The results show that toxicity decreased as the concentration of the NAALADase inhibitor increased, suggesting that the compounds of the present invention would be effective in treating ischemia or neuronal damage caused by ischemia.

The methods for this assay are described in detail below. Specifically, cell cultures were exposed to potassium cyanide and 2-deoxyglucose (2-DG) (10 mM) and analyzed for release of lactate dehydrogenase (LDH).

In Vitro Toxicity of NAAG

To examine the effect of NAAG on in vitro toxicity, cortical cell cultures were treated with NAAG (in concentrations ranging from 3 μM to 3 mM) for 20 minutes. The toxicity measurement for each concentration of NAAG is provided in TABLE VI below and graphically represented in FIG. 2.

TABLE VI

| Dose of NAAG | % Toxicity |
| --- | --- |
| 3 μM | 3.51 (n = 1) |
| 10 μM | 4.30 ± 3.12 (n = 3) |
| 30 μM | 11.40 ± 6.17 (n = 3) |
| 100 μM | 12.66 ± 5.50 (n = 3) |
| 300 μM | 13.50 ± 4.0 (n = 3) |
| 1 mM | 21.46 ± 4.20 (n = 3) |
| 3 mM | 45.11 ± 4.96 (n = 3) |

The results show that toxicity increased as the concentration of NAAG increased. The toxicity is attributed to the release of glutamate by NAAG when cleaved by NAALADase.

In Vitro Toxicity of NAAG following Treatment with NAALADase Inhibitors

To examine the effect of NAALADase inhibitors on in vitro glutamate toxicity, cortical cell cultures were treated with 2-(phosphonomethyl)pentanedioic acid (1 μM) during exposure to NAAG and for one hour thereafter. The toxicity measurement for each concentration of NAAG is provided in TABLE VII below and graphically represented in FIG. 3.

TABLE VII

| Dose of NAAG | % Toxicity |
| --- | --- |
| 3 μM | −4.71 (n = 1) |
| 10 μM | −3.08 ± 0.81 (n = 3) |
| 30 μM | −4.81 ± 1.13 (n = 3) |
| 100 μM | −2.87 ± 0.78 (n = 3) |
| 300 μM | −2.09 ± 0.48 (n = 3) |
| 1 mM | 0.26 ± 1.11 (n = 3) |
| 3 mM | 16.83 ± 8.76 (n = 3) |

Figure 2:
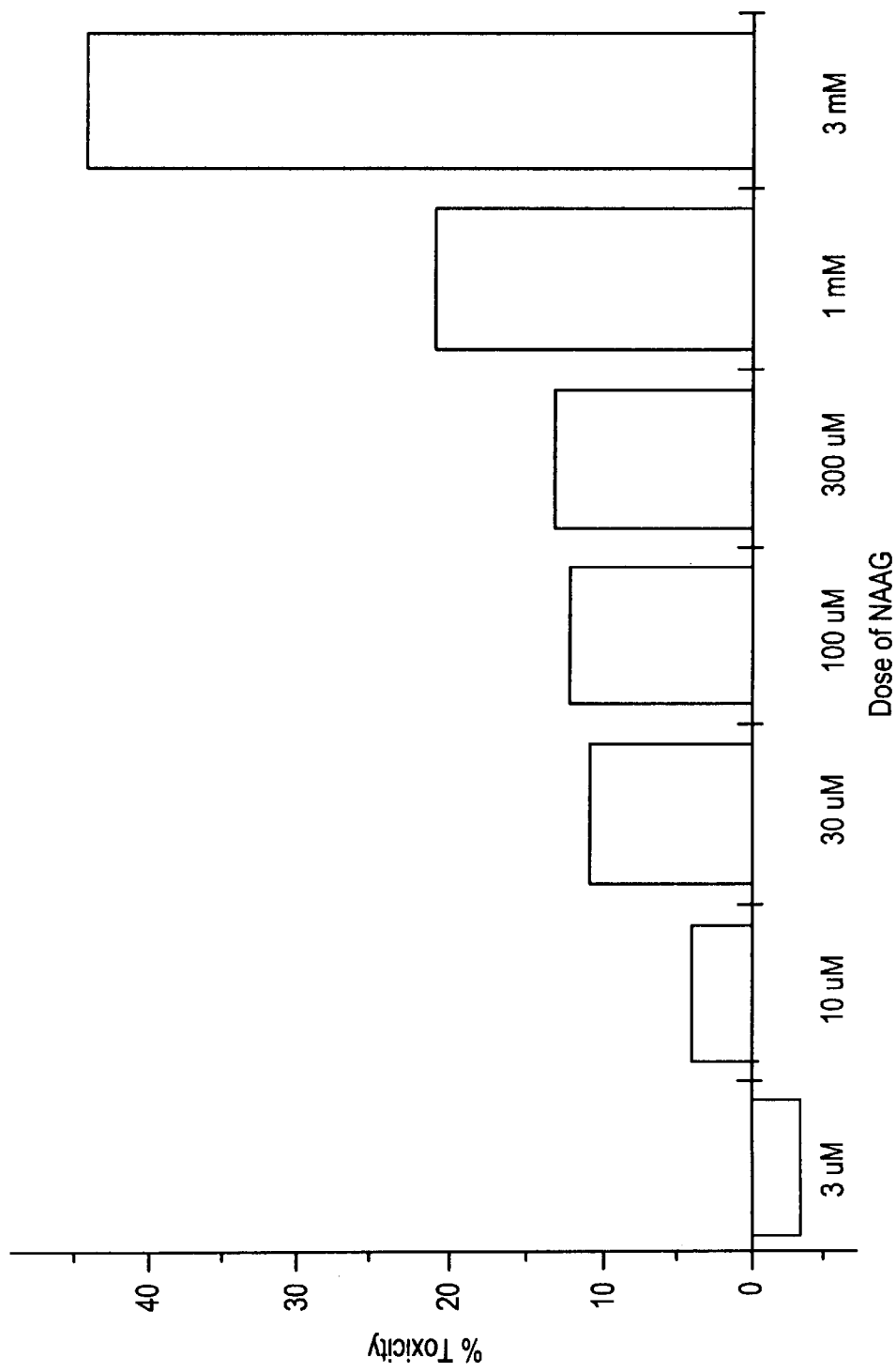
FIG. 2 is a bar graph plotting in vitro toxicity against various doses of NAAG to which cortical cell cultures were exposed.
Figure 3:
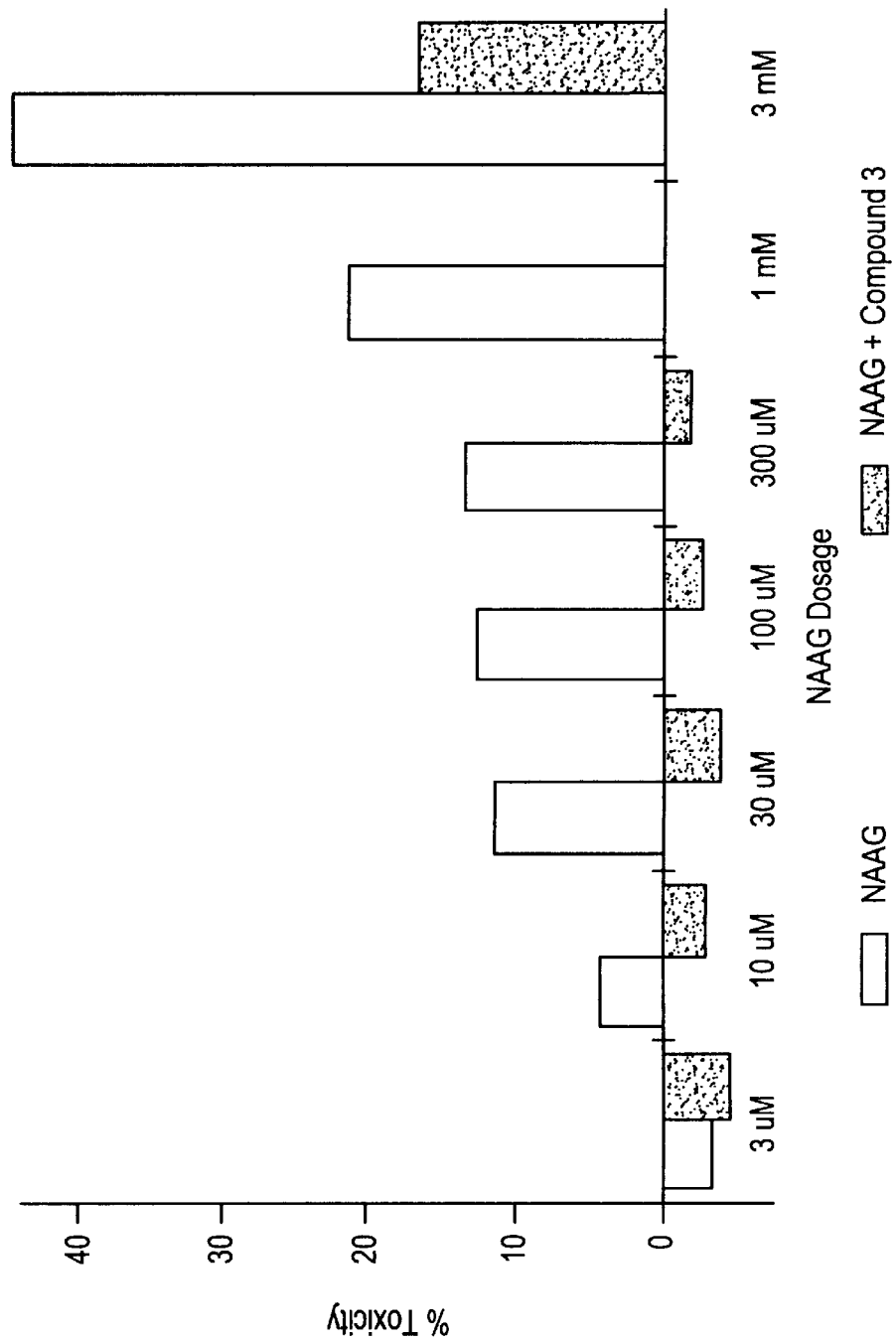
FIG. 3 is a bar graph plotting in vitro toxicity following treatment with 2-(phosphonomethyl)pentanedioic acid, against various doses of NAAG to which cortical cell cultures were exposed.

When compared to the results of FIG. 2/TABLE VI, the results of FIG. 3/TABLE VII show that toxicity decreased considerably after treatment with the NAALADase inhibitor, suggesting that the compounds of the present invention would be effective in treating glutamate abnormalities.

In Vitro Assay of NAALADASE Inhibitors on Ischemia—with Delayed Treatment

Figure 4:
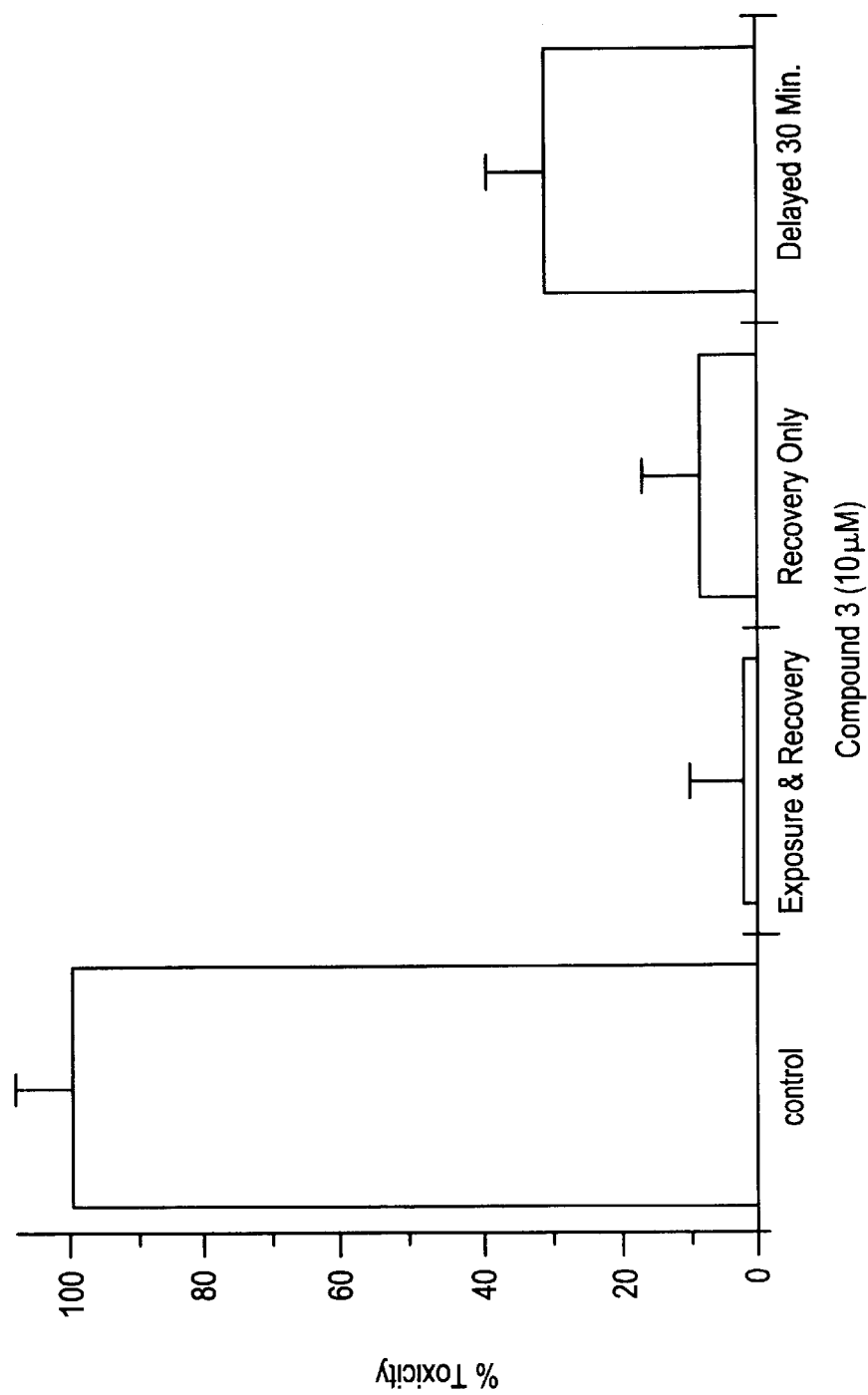
FIG. 4 is a bar graph plotting in vitro toxicity of ischemic insult against various times at which 2-(phosphonomethyl)pentanedioic acid is administered to cortical cell cultures.

To examine the effect of NAALADase inhibitors on in vitro toxicity following ischemia, cortical cell cultures were treated with 2-(phosphonomethyl)pentanedioic acid (i) during an ischemic insult and for one hour thereafter (exposure and recovery); (ii) for one hour following ischemic insult (recovery only); and (iii) for one hour beginning 30 minutes after ischemic insult (delayed 30 minutes). The toxicity measurement for each time of administration is provided in TABLE VIII below and graphically represented in FIG. 4.

TABLE VIII

| Time of Administration Relative to Ischemic Insult | % Toxicity |
| --- | --- |
| Control | 100.00% |
| Exposure & Recovery | 2.54% |

TABLE VIII-continued

| Time of Administration Relative to Ischemic Insult | % Toxicity |
| --- | --- |
| Recovery Only | 9.03% |
| Delayed 30 Minutes | 31.49% |

The results show that significant neuronal protection is achieved when NAALADase inhibitors are administered during exposure and recovery from an ischemic insult, and even after a 30 minute delay following the ischemic insult.

Protocol for In Vitro Toxicity Assay a. Cell Culture

Dissociated cortical cell cultures are prepared using the papain-dissociation method of Heuttner and Baughman (1986) as modified by Murphy and Baraban (1990). See TABLE IX for the Dissociated Culture Protocol as used herein. Fetuses of embryonic day 17 are removed from timed pregnancy rats (Harlan Sprague Dawley). The cortex is rapidly dissected out in Dulbecco's phosphate-buffered saline, stripped of meninges, and incubated in a papain solution for 15 min at 37° C. The tissue is then mechanically triturated and pelleted at 500 g (1000–2000 rpm on swinging bucket Beckman). The pellet is resuspended in a DNAase solution, triturated with a 10 ml pipette x15–20, layered over a "10×10" solution containing albumin and trypsin inhibitor (see TABLE IX for an example of a "10×10" solution), repelleted, and resuspended in a plating medium containing 10% fetal bovine serum (HyClone A-1111-L), 5% heat-inactivated Equine serum (HyClone A-3311-L), and 84% modified Earle's basal medium (MEM) (Gibco 51200-020) with high glucose (4.5 g/L), and 1 g/L $NaHCO_3$. Each 24-well plate is pretreated with poly-D-lysine (0.5 ml/well of 10 μg/ml) for 1 h and rinsed with water before plating. Cultures are plated at $2.5 \times 10^6$ cells/ml with each well of a 24 well plate receiving 500 μl/well. Alternatively, 35 mm dishes can be plated at 2 ml/dish, 6 well plates at 2 ml/well, or 12 well plates at 1 ml/well. After plating, 50% of the medium is changed every 3–4 days with growth serum containing 5% heat-inactivated Equine serum (HyClone A-3311-L), 95% modified Earle's basal medium (MEM) (Gibco 51200-020), and 1% L-Glutamine (Gibco 25030-081). Experiments are performed after 21 days in cultures. Cultures are maintained in a 5% $CO_2$ atmosphere at 37° C. These methodologies are described in further detail in the TABLE IX below.

TABLE IX

DISSOCIATED CULTURE PROTOCOL

I. PREPARE SOLUTIONS
Stocks/Solutions

| DNAase Stock, 1 ml (100x) | Dulbecco's PBS, 500 ml |
| --- | --- |
| 5 mg DNAase I (Worthington LS002004); 1 ml dissoc. EBSS; freeze as 50 μl aliquots. | 4 gm NaCl (J. T. Baker 3624–01) 1.06 gm $Na_2HPO_4 \cdot 7H_2O$ (Fisher S373–3); 100 mg KCl (Fisher P217–500) 100 mg $KH_2PO_4$ (Sigma P-0662) 500 ml $dH_2O$; adjust pH to 7.4 and sterile filter. |

TABLE IX-continued

DISSOCIATED CULTURE PROTOCOL

| Dissociated EBSS, 500 ml | EDTA Stock, 10 ml |
|---|---|
| 1.1 gm NaHCO₃;<br>50 ml EBSS stock (Gibco 14050–025);<br>450 ml dH₂O;<br>sterile filter. | 184.2 mg EDTA sodium salt (Sigma ED4S);<br>10 ml dH₂O;<br>sterile filter. |
| 10 and 10 Stock, 10 ml | Poly-D-Lysine Stock, 5 ml |
| 100 mg BSA (Sigma A-4919);<br>100 mg Trypsin Inhibitor from Egg White (Sigma T-2011);<br>10 ml dissoc. EBSS;<br>sterile filter.<br>Media | 5 mg Poly-D-Lysine, 100–150 K (Sigma P-6407)<br>5 ml sterile water;<br>keep frozen. |
| Dissociated growth, 500 ml | Plating media, 300 ml |
| 500 ml MEM (Gibco 51200–020) containing glucose and NaHCO₃ (2.25 gm glucose and 0.5 gm NaHCO₃);<br>25 ml heat-inactivated Equine Serum (HyClone A-3311-L);<br>5 ml L-Glutamine (200 mM, 100x stock, Gibco 25030–081);<br>sterile filter.<br>15 ml heat-inactivated Equine Serum (HyClone A-3311-L);<br>3 ml L-Glutamine (200 mM, 100x stock, Gibco 25030–081); (Gibco 15140–015);<br>1 ml Penicillin-Streptomycin stock. | 250 ml MEM containing glucose and sodium bicarbonate (2.25 gm glucose and 0.5 gm NaHCO₃ in 500 ml Gibco MEM 51200–020);<br>30 ml Fetal Bovine Serum (HyClone A-1111-L). |
| For papain dissociation: | For DNAase treatment: |
| 4 mg Cysteine (0–8277); | DNAase, 5 ml |
| 25 ml dissoc. EBSS;<br>250 μl Papain stock (Worthington LS003126);<br>place in 37° C. waterbath until clear. | 4.5 ml dissoc. EBSS;<br>500 μl "10 and 10" stock;<br>50 μl DNAase stock.<br>"10 and 10", 5 ml<br>4.5 ml of EBSS;<br>500 μl "10 and 10" stock. |

II. COAT DISHES

Use poly-d-lysine stock at 1:100 dilution to coat 24-well plates (0.5 ml/well) or at 1:10 dilution to coat 35 mm glass cover slips (1.0 ml/coverslip)
Leave until end of dissection.

III. DISSECT TISSUE

Use Harlan Sprague-Dawley timed pregnancy rats, ordered to arrive at E-17.
Decapitate, spray abdomen down with 70% EtOH.
Remove uterus through midline incision and place in sterile dPBS.
Remove brains from embryos, leaving them in dPBS.
Brain removal: Penetrate skull and skin with fine forceps at lambda. Pull back to open posterior fossa.
Then move forceps anteriorly to separate sagittal suture. Brain can be removed by scooping back from olfactory bulbs under the brain.
Move brains to fresh dPBS; subsequently, dissect away from cortex.

IV. PAPAIN DISSOCIATION

Transfer cortices equally to two 15 ml tubes containing sterile papain solution, maintained at 37° C.
Triturate x1 with sterile 10 ml pipette.
Incubate only for 15 minutes at 37° C.
Spin at 500 G for 5 minutes (1000–2000 RPM on swinging bucket Beckman)

V. DNAase TREATMENT

Remove supernatant and any DNA gel layer from cell pellet (or pick up and remove pellet with pipette)
Move cell pellet to DNAase solution.
Triturate with 10 ml pipette, x15–20.
Layer cell suspension over the "10 and 10" solution by pipetting it against the side of the tubes.
Spin again at 500 G for 5 minutes (cells will spin into "10 and 10" layer)
Wash tube sides with plating media without disturbing pellet.
Pipette off the media wash and repeat the wash.

VI. PLATE

Add about 4.5 ml plating media to each pellet for 5 ml volume.
Re-suspend with 10 ml pipette.
Pool cells into a single tube.
Quickly add 10 μl of the suspended cells to a hemocytometer so that they do not settle.
Count cells per large square, corresponding to 10 million cells/ml.
Put re-suspended cells into a larger container so that they number 2.5 million cells/ml.
Triturate to homogeneity.
Finish coating plates:
Aspirate or dump Lysine;
Wash x1 with sterile water and dump.
Add plating media, with cells, to the plates as follows:

| 35 mm dishes | 2 ml/dish; |
|---|---|
| 6 well plate | 2 ml/well; |
| 12 well plate | 1 ml/well; |
| 24 well plate | 500 ml/well. |

VII. FEED

Cultures are usually made on Thursdays.
Start feeding twice a week; beginning the following Monday, feedings on Mondays and Fridays.
Remove 50% of volume and replace with fresh growth media.

b. Ischemic Insult using potassium cyanide and 2-deoxyglucose

Twenty-one to twenty-four days following the initial cortical cell plating, the experiment is performed. The cultures are washed three times in HEPES buffered saline solution containing no phosphate. The cultures are then exposed to potassium cyanide (KCN) (5 mM) and 2-deoxyglucose (2-DG) (10 mM) for 20 minutes at 37° C. These concentrations were shown previously to induce maximal toxicity (Vornov et al., J. Neurochem, 1995, Vol. 65, No. 4, pp. 1681–1691). At the end of 24 hours, the cultures are analyzed for release of the cytosolic enzyme lactate dehydrogenase (LDH), a standard measure of cell lysis. LDH measurements are performed according to the method of Koh and Choi (J. Neuroscience Methods, 1987).

C. NAAG Induced Neurotoxicity

Cultures are assessed microscopically and those with uniform neuronal densities are used in the NAAG neurotoxicity trials.

At the time of the experiment, the cultures are washed once in HEPES-buffered saline solution (HBSS; NaCl 143.4 mM, HEPES 5 mM, KCl 5.4 mM, MgSO₄ 1.2 mM, NaH₂PO₄ 1.2 mM, CaCl₂ 2.0 mM, D-glucose 10 mM) (Vornov et al., 1995) and then exposed to various concentrations of NAAG for 20 minutes at 37° C. NAAG concentrations range from 3 μM to 3 mM, and include 3 μM, 10 μM, 30 μM, 100 μM, 300 μM, 1 mM, and 3 mM. At the end of exposure, the cells are washed once with HEPES buffered saline solution and then replaced with serum free modified Earle's basal medium. The cultures are then returned to the $CO_2$ incubator for 24 hour recovery.

d. Lactate Dehydrogenase Assay

Release of the cytosolic enzyme lactate dehydrogenase (LDH), a standard measure of cell lysis, is used to quantify injury (Koh and Choi, 1987). LDH-activity measurements are normalized to control for variability between culture preparations (Koh et al., 1990). Each independent experiment contains a control condition in which no NAALADase inhibitors are added; a small amount of LDH activity is found in these controls. This control measurement is subtracted from each experimental point. These values are normalized within each experiment as a percentage of the injury caused by NAAG/ischemia. Only main effects of NAALADase inhibitors are considered; interactions between dose and condition are not examined statistically.

A measurement of the potency of each compound tested is made by measuring the percentage of LDH release into the growth media after exposure to NAAG/ischemia plus NAALADase inhibitor or NAAG/ischemia plus saline (control). Since high concentrations of glutamate may be toxic to cells in certain circumstances, measurement of glutamate toxicity is observed using LDH as a standard measurement technique.

In Vivo Assay of NAALADase Inhibitors on Infarct Volume

To examine the in vivo effect of NAALADase inhibitors on infarct volume, injury to the cortex was evaluated in three groups of rats following middle cerebral artery occlusion. In the control group, the rats received saline. In another group, the rats received 10 mg/kg of 2-(phosphonomethyl)pentanedioic acid followed by 2 mg/kg/hr of 2-(phosphonomethyl)pentanedioic acid for 1 hour. In the final group, the rats received 100 mg/kg of 2-(phosphonomethyl)pentane-dioic acid followed by 20 mg/kg/hr of 2-(phosphonomethyl)pentanedioic acid for one hour.

Figure 5:
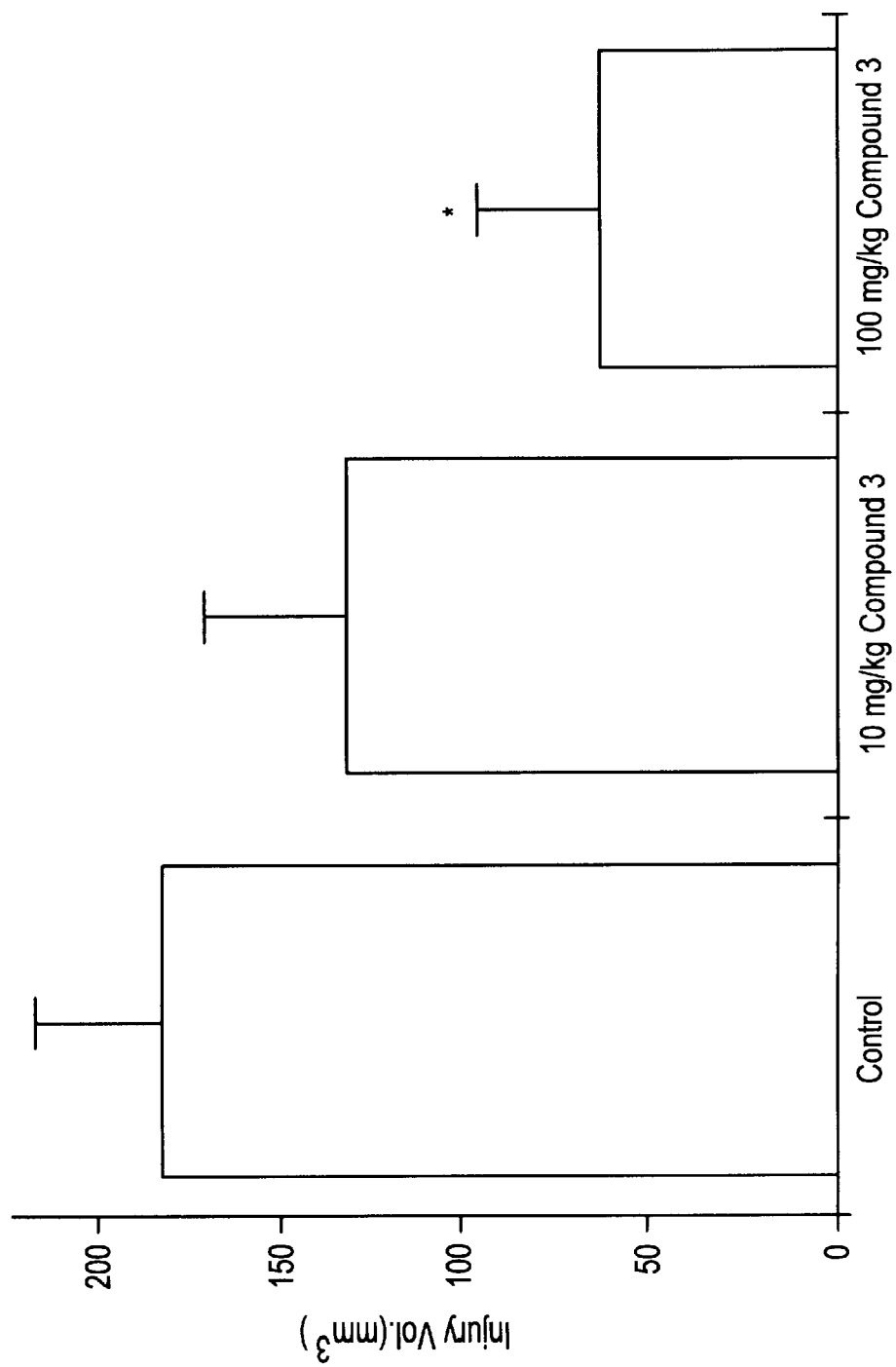
FIG. 5 is a bar graph plotting in vivo cortical injury volume against various doses of 2-(phosphonomethyl)pentanedioic acid with which rats were treated following middle cerebral artery occlusion.

The cortical injury volume for each group of rats is provided in TABLE X below and graphically represented in FIG. 5.

TABLE X

| Cortical Injury Volume (mm³) ± S.E.M. | |
| --- | --- |
| Control | 184.62 ± 33.52 (n = 10) |
| 10 mg/kg | 135.00 ± 32.18 (n = 10) |
| 100 mg/kg | 65.23 ± 32.18 (n = 10) |
| Cortical Injury Volume (% injury) ± S.E.M. | |
| Control | 34.44 ± 6.53 (n = 10) |
| 10 mg/kg3 | 29.14 ± 7.68 (n = 10) |
| 100 mg/kg | 13.98 ± 6.64 (n = 10) |
| Cortical Protection (% protection) | |
| Control | 0% |
| 10 mg/kg | 27% |
| 100 mg/kg | 65% |

The results show that cortical injury volume decreased and cortical protection increased as the amount of NAALADase inhibitor increased, further supporting the neuroprotective effects of the compounds of the present invention.

Protocol for In Vivo Cortical Injury Assay A colony of SHRSP rats is bred at Johns Hopkins School of Medicine from three pairs of male and female rats obtained from the National Institutes of Health (Laboratory, Sciences Section, Veterinary Resources Program, National Center for Research Resources, Bethesda, Md.). All rats are kept in a virus-free environment and maintained on regular diet (NIH 31, Zeigler Bros, Inc.) with water ad libitum. All groups or rats are allowed to eat and drink water until the morning of the experiment.

Transient occlusion of the middle cerebral artery (MCA) is induced by advancing a 4-0 surgical nylon suture into the internal carotid artery (ICA) to block the origin of the MCA (Koizumi, 1986; Longa, 1989; Chen, 1992). Briefly, animals are anesthetized with 4% halothane, and maintained with 1.0 to 1.5 % halothane in air enriched oxygen using a face mask. Rectal temperature is maintained at 37.0+0.5° C. throughout the surgical procedure using a heating lamp. The right femoral artery is cannulated for measuring blood gases (pH, oxygen tension [$PO_2$], carbon dioxide tension [$PCO_2$]) before and during ischemia, for monitoring blood pressure during the surgery. The right common carotid artery (CCA) is exposed through a midline incision; a self-retraining retractor is positioned between the digastric and mastoid muscles, and the omohyoid muscle is divided. The right external carotid artery (ECA) is dissected and ligated. The occipital artery branch of the ECA is then isolated and coagulated. Next, the right internal carotid artery (ICA) is isolated until the pterygopalatine artery is exposed, and carefully separated from the adjacent vagus nerve. The pterygopalatine artery is ligated with 4-0 silk suture close to its origin.

After the CCA is ligated with 4-0 silk suture, a 4-0 silk suture to prevent bleeding from a puncture site, through which a 2.5 cm length of 4-0 monofilament nylon suture (Ethilon), its tip rounded by heating near a electric cautery, is introduced into the ICA lumen. A 6-0 silk suture is tightened around the intraluminal nylon suture at the bifurcation to prevent bleeding, and the stretched sutures at the CCA and the ICA are released. The nylon suture is then gently advanced as far as 20 mm.

Anesthesia is terminated after 10 minutes of MCA occlusion in both groups, and animals awakened 5 minutes thereafter. After 2 hours of ischemia, anesthesia is reanesthetized, and reperfusion is performed by withdrawing the intraluminal nylon suture until the distal tip became visible at the origin of the ICA.

Arterial pH and $PaCO_2$, and partial pressure of oxygen ($PaO_2$) are measured with a self-calibrating Radiometer electrode system (ABL 3; Copenhagen, Denmark). Hemoglobin and arterial oxygen content are measured with a hemoximeter (Radiometer, Model OSM3; Copenhagen, Denmark). Blood glucose is measured with a glucose analyzer (model 2300A, Yellow Springs Instruments, Yellow Springs, Ohio).

Each group is exposed to 2 hours of right MCA occlusion and 22 hours of reperfusion. All variables but the rectal temperature are measured at baseline, at 15 minutes and 45 minutes of right MCA occlusion. The rectal temperature is measured at baseline, at 0 and 15 min of MCA occlusion, and at 0 and 22 hours of reperfusion.

In Vitro Assay of NAALADase Inhibitors on Cancer

Figure 6:
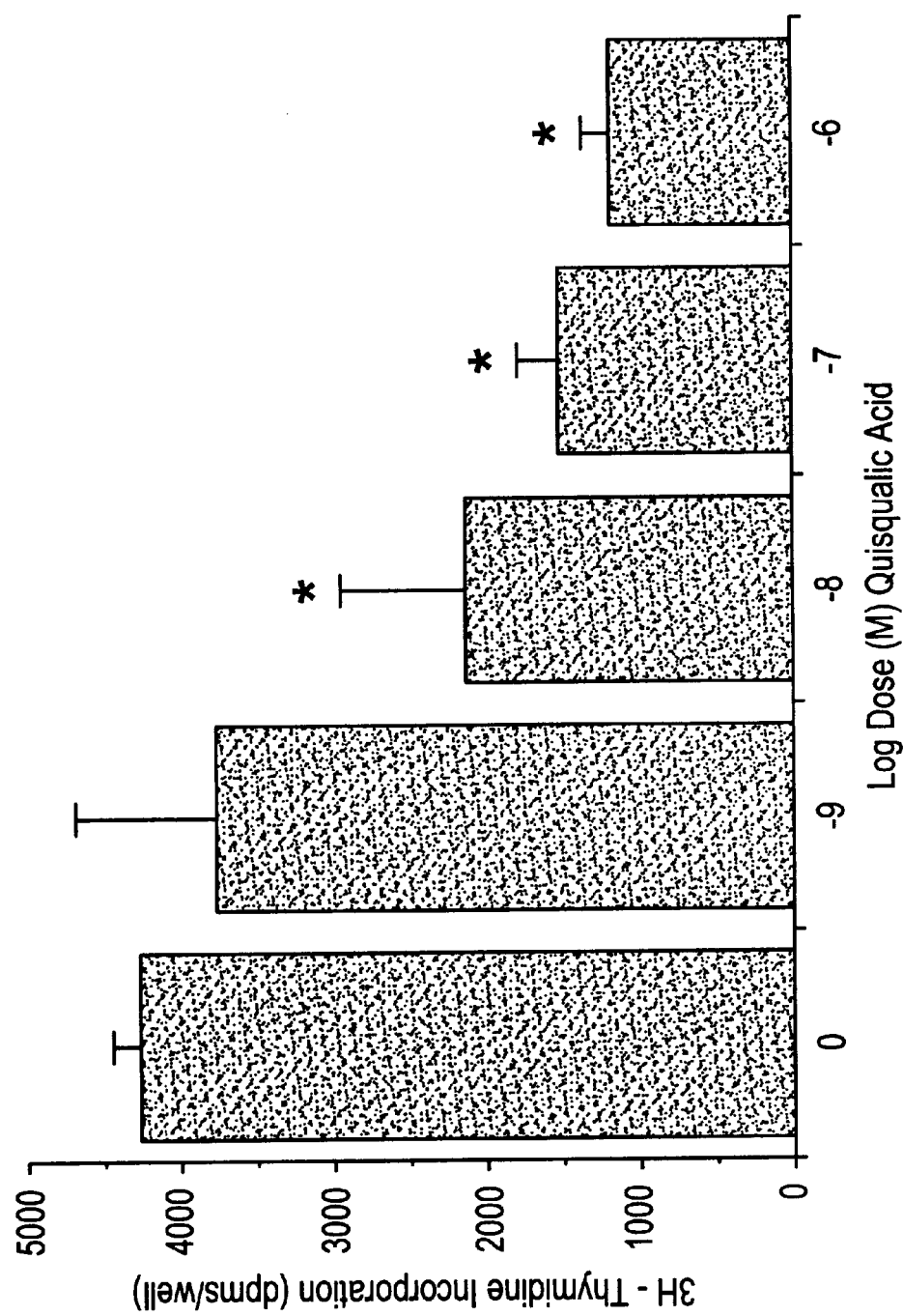
FIG. 6 is a bar graph plotting in vitro cancer cell growth against various doses of quisqualic acid with which LNCAP cells were treated.
Figure 7:
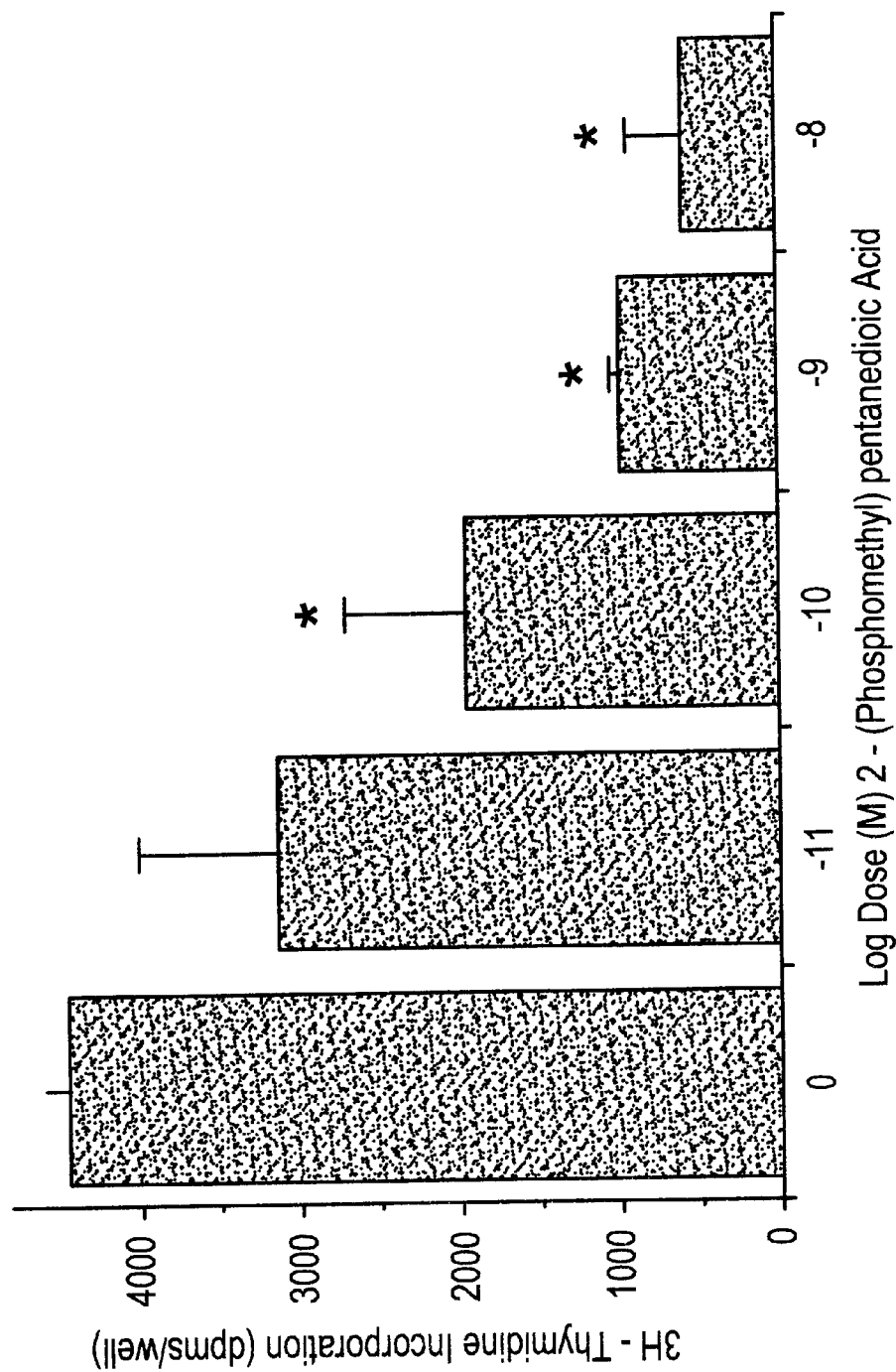
FIG. 7 is a bar graph plotting in vitro cancer cell growth against various doses of 2-(phosphonomethyl)pentanedioic acid with which LNCAP cells were treated.

To examine the effect of NAALADase inhibitors on cancer cell line, LNCAP cells (a prostate cancer cell line) were treated with quisqualate acid (in concentrations ranging from 10 nM to 1 μgM) and 2-(phosphonomethyl) pentanedioic acid (in concentrations ranging from 100 pM to 10 nM). The 3H-thymidine measurement for each concentration of quisqualate acid and 2-(phosphonomethyl) pentanedioic acid is provided in TABLE XI below and graphically represented in FIGS. 6 and 7, respectively.

TABLE XI

| | 3H-Thymidine Incorporation (dpm/well) | |
| --- | --- | --- |
| Dose | Quisqualic Acid | 2-(phosphonomethyl)-pentanedioic acid |
| Control | 4813 ± 572 | 4299 ± 887 |
| 10 pM | — | 3078 ± 1006 |
| 100 pM | — | 2062 ± 595 |
| 1 nM | 3668 ± 866 | 1001 ± 52 |
| 10 nM | 2137 ± 764 | 664 ± 366 |
| 100 nM | 1543 ± 312 | — |
| 1 μM | 1295 ± 181 | — |

The results show that LNCAP cell proliferation (as measured by the incorporation of 3H-thymidine) decreased significantly as the concentration of the NAALADase inhibitors increased, suggesting that the compounds of the present invention would be effective in treating cancer, particularly prostate cancer.

Protocol for In Vitro Cancer Assay

Cells in RPMI 1640 medium containing 10% Fetal Calf Serum (FCS) are plated in 24 well plates and allowed to adhere for 24 hours before addition of quisqualic acid ($10^{-9}$ to $10^{-6}$) or 2-(phosphonomethyl)pentanedioic acid ($10^{-11}$ to $10^{-8}$) for 7 days. On the 7th day, the cells are pulsed with 3H-thymidine for 4 hours, harvested and measured for radioactivity. Values represent means±SEM of 6 separate cell wells for each treatment. All experiments are performed at least twice.

To control for non-specific cytostatic effects of quisqualate acid and 2-(phosphonomethyl)pentanedioic acid, the agents are simultaneously evaluated on a non-NAALADase containing prostate cell line, DU145 (Carter et al., Proc. Natl. Acad. Sci. U.S.A., (93) 749–753, 1996). If the treatments with quisqualate acid and 2-(phosphonomethyl) pentanedioic have no significant effect on cell growth, the NAALADase inhibiting activity of the agents are uniquely responsible for their cytostatic effects on prostate carcinoma cell lines.

Cell Lines and Tissue Culture

LNCAP cells are obtained from Dr. William Nelson at the Johns Hopkins School of Medicine in Baltimore, Md. DU145 cells are obtained from American Type Culture Collection (Rockville, Md.). Cells are grown in RPMI-1640 media supplemented with 5% heat-inactivated fetal calf serum, 2 mM-glutamine, 100 units/ml penicillin, and 100 μg/ml streptomycin (Paragon) in a humidified incubator at 37° C. in a 5% $CO_2$/95% air atmosphere.

[3H] Thymidine Incorporation Assays

The cells are suspended at $1\times10^3$ cells/ml in RPMI-1640 media and seeded into 24-well plates at 500 μl per well. After 24 hour incubation, various concentrations of quisqualic acid (Sigma) or the potent NAALADase inhibitor 2-(phosphonomethyl)pentanedioic acid (synthesized according to the methods of Jackson et al., J Med Chem 39(2) 619–622) is added to the wells and the plates are returned to the incubator. On days 3, 5 and 7, media and drug are refreshed. On the 8th day following seeding, each well is pulsed with 1 μCi 3H-thymidine (New England Nuclear) for 4 hours. Media is then removed and the wells washed 2 times with phosphate buffered saline (pH=7.4). The contents of each well is subsequently solubilized 250 μl of 0.2 N NaOH and transferred to scintillation vials. 5 ml UltimaGold (Packard) scintillation cocktail is added and radioactivity is quantitated using a Beckman LS6001 scintillation counter.

The purity and/or identity of all synthetic compounds is ascertained by thin layer chromatography, High Pressure Liquid Chromatography (HPLC), mass spectrometry, and elemental analysis. Proton Nuclear Magnetic Resonance (NMR) spectra are obtained using a Bruker spectrometer. Chemical shifts are reported in parts per million relative to tetramethylsilane as internal standard. Analytical thin-layer chromatography (TLC) is conducted on prelayered silica gel GHLF plates (Analtech, Newark, Del.). Visualization of the plates is accomplished by using UV light, phosphomolybdic acid-ethanol, and/or iodoplatinate charring. Flash chromatography is conducted on Kieselgel 60, 230–400 mesh (E. Merck, Darmstadt, West Germany). Solvents are either reagent or HPLC grade. Reactions are run at ambient temperature and under a nitrogen atmosphere unless otherwise noted. Solutions are evaporated under reduced pressure on a Buchi rotary evaporator.

EXAMPLES

The following examples are illustrative of the present invention and are not intended to be limitations thereon. Unless otherwise indicated, all percentages are based upon 100% by weight of the final composition.

Example 1

Synthesis of 2-benzyl-3-phosphonopropanoic acid

Synthesis of 2-benzylacrylic acid

To a cooled (0° C.) mixture of benzyl malonic acid (3.37 g, 17.4 mmol) and diethylamine (1.34 g, 18.3 mmol) in water (10 ml) was added formaldehyde (37% solution in water, 2.1 g, 26.1 mmol) with stirring. The reaction was allowed to warm to room temperature and after 2 hours heated to reflux. After 16 hours, the reaction mixture was cooled to room temperature, then made acidic with hydrochloric acid. The mixture was extracted twice with ethyl acetate. The ethyl acetate layers were combined and dried over sodium sulfate, then the solvent was removed under reduced pressure. The resulting residue was purified by column chromatography to yield 2.2 g (78%) of white solid. $^1$H NMR (CDCl$_3$): δ 3.7 (s, 2H), 5.6 (s, 1H), 6.4 (s, 1H), 7.1–7.4 (m, 5H)

Synthesis of benzyl 2-benzylacrylate

To a solution of 2-benzylacrylic acid (1.02 g, 6.3 mmol) in dimethylformamide (10 ml) was added potassium carbonate (1.04 g, 7.6 mmol) and water (0.25 ml) with stirring. After 10 minutes, benzyl bromide (0.9 ml, 7.6 mmol) was added. After 3 hours, water was added and the resulting mixture was extracted with ether. The ether layer was washed 3 times with water, dried over magnesium sulfate, filtered over silica gel, and concentrated under reduced pressure. The resulting oil was distilled (70° C., 0.2 torr) to remove any unreacted starting material, then distilled (125° C., 0.2 torr) to yield 1.38 g (87%) of clear oil. $^1$H NMR (CDCl$_3$): δ 3.7 (s, 2H), 5.2 (s, 2H), 5.5 (s, 1H), 6.3 (s, 1H), 7.2–7.6 (m, 10H).

Synthesis of benzyl 3-(dibenzyloxyphosphono)-2-benzylpropanoate

To a mixture of benzyl 2-benzylacrylate (6.4 g, 25.4 mmol) and dibenzylphosphite (7.3 g, 27.9 mmol) was added potassium carbonate (6.1 g, 44.2 mmol) and tetra-n-butylammonium hydrogen sulfate (1.8 g, 5.3 mmol) with stirring. The resulting mixture was heated to 100° C. After 16 hours, the reaction mixture was cooled to room temperature and poured into dilute hydrochloric acid (5%) and the aqueous mixture was extracted twice with ethyl acetate. The ethyl acetate extracts were combined, dried over magnesium sulfate and concentrated under reduced pressure. The resulting residue was purified by column chromatography to yield 5.2 g (40%) of clear oil. $^1$H NMR (CDCl$_3$): δ 1.8–2.0 (ddd, 1H) 2.2–2.4 (ddd, 1H), 2.8–2.9 (dd, 1H), 2.9–3.0 (dd, 1H), 3.1 (m, 1H), 4.7–5.0 (m, 6H), 7.0–7.4 (m, 20H).

Synthesis of 2-benzyl-3-phosphonopropanoic acid

A mixture of dibenzyl 3-(dibenzyloxyphosphono)-2-benzylpropanoate (1.5 g, 2.9 mmol), palladium on carbon catalyst (10%, 0.5 g) and water (25 ml) was shaken under hydrogen (60 psi) for 16 hours. The reaction mixture was filtered over celite and the filtrate was lyophilized to yield the desired product as white crystals.

Example 2

Synthesis of 2-(2-phenylethyl)-3-phosphonopropanoic acid

This compound was prepared in a manner similar to that as described above in Example 1 with the following exceptions.

Synthesis of diethyl 2-phenylethyl malonate

Sodium ethoxide (12.7 g, 187 mmol) was dissolved in ethanol (200 ml) with heat (50° C.) and stirring. To the resulting solution was added diethyl malonate (30 g, 187 mmol) and the solution was heated to reflux. While still refluxing, 2-bromoethylbenzene (34.7 g, 187 mmol) was added dropwise to the reaction mixture. After 8 hours, the reaction mixture was cooled to room temperature. The reaction mixture was filtered and the filtrate was concentrated under reduced pressure. The resulting residue was dissolved in ether and washed twice with water. The organic layer was dried over magnesium sulfate, then concentrated under reduced pressure. The resulting oil was distilled (0.5 torr, 90° C.) to remove any unreacted starting material, then distilled (0.5 torr, 120° C.) to yield 25 g (51%) of clear oil. $^1$H NMR (CDCl$_3$): δ 1.2 (t, 6H), 2.2 (q, 2H), 2.5 (t, 2H), 3.3 (t, 1H), 4.2 (q, 4H), 7.1–7.3 (m, 5H).

Synthesis of 2-phenylethyl malonic acid

To a cooled (0° C.) solution of diethyl 2-ethylphenyl malonate (6.8 g, 25.8 mmol) in ethanol (15 ml), was added a cooled (0° C.) solution of potassium hydroxide (4.3 g, 77.3 mmol) in water (50 ml) with stirring. After several hours, the reaction mixture was concentrated under reduced pressure to remove the ethanol, and the remaining aqueous solution was made acidic with hydrochloric acid. The mixture was extracted twice with ethyl acetate. The ethyl acetate layers were combined, dried over magnesium sulfate, then filtered over silica gel. The ethyl acetate was removed under reduced pressure to yield 4.6 g (87%) of white solid. $^1$H NMR (d6-DMSO): δ 2.0 (q, 2H), 2.6 (t, 2H), 3.3 (t, 1H), 7.2–7.5 (m, 5H), 12.8 (b, 2H).

Synthesis of 2-(2-phenylethyl)-3-phosphonopropanoic acid

The remaining steps are the same as that described in Example 1. $^1$H NMR (d6-DMSO): δ 1.5–1.9 (m, 3H), 2.1 (m, 1H) , 2.4 (t, 2H), 2.6 (m, 1H), 6.8–7.0 (m, 5H) Anal. Calcd. for C$_{11}$H$_{15}$PO$_5$—0.2 H$_2$O: C, 50.46; H, 5.93. Found: C, 50.44; H, 5.92.

Example 3

Synthesis of 2-methyl-3-phosphonopropanoic acid

This compound was prepared in a manner similar to that as described above in Example 2. $^1$H NMR (d6-DMSO): β 1.2 (d, 3H), 1.7–1.8 (td, 1H), 2.0–2.1 (td, 1H), 2.7 (m, 1H). Anal. Calcd. for C$_4$H$_9$PO$_5$—0.7 H$_2$O: C, 26.59; H, 5.80. Found: C, 26.53; H, 5.55.

Example 4

Synthesis of 2-O-(phenylphosphonomethyl)pentanedioic acid

Synthesis of dibenzyl 2-(hydrohydroxyphosphorylmethyl) pentanedioate

To a mixture of dry phosphinic acid (100 g, 1520 mmol) in chloroform (100 ml) was added triethylamine (213 ml, 1520 mmol) with mechanical stirring. Additional chloroform (650 ml) was added and the resulting mixture was cooled (0° C.). Additional triethylamine (382 ml, 2720 mmol) was added followed by trimethylsilyl chloride (328 ml, 2580 mmol) while maintaining the temperature of the reaction mixture at 0° C. A solution of 2-methylenepentanedioate (70 g, 220 mmol) in chloroform (150 ml) was added to the reaction mixture. The reaction mixture was allowed to warm to room temperature. After 6 hours the aqueous layer was extracted with chloroform and the combined chloroform layers were dried over magnesium sulfate. The chloroform was removed under reduced pressure and the resulting yellow oil was purified by column chromatography to yield 40 g (47%) of clear oil.

Synthesis of dibenzyl 2-(benzyloxyhydrophosphorylmethyl) pentanedioate

To a solution of dibenzyl 2-(hydrohydroxyphosphorylmethyl)pentanedioate (19.3 g, 49.4 mmol) in tetrahydrofuran (110 ml) was added benzyl alcohol (5.1 ml, 49.4 mmol), 4-dimethylaminopyridine (0.5 g, 4.1 mmol) and dicyclohexylcarbodiimide (12.0 g, 58.2 mmol) After 30 minutes, the reaction mixture was filtered and the tetrahydrofuran was removed under reduced pressure. The resulting residue was purified by column chromatography to yield 11.5 g (47%) of clear oil.

Synthesis of dibenzyl 2-(benzyloxyhydroxyphosphonomethyl)pentanedioate

To a solution of dibenzyl 2-(benzyloxyhydrophosphorylmethyl)pentanedioate (10 g, 21.6 mmol) dioxdioxane was added a solution of sodium periodate (5.1 g, 23.8 mmol) in water (50 ml) with stirring. After 16 hours, ethyl acetate was added to the reaction mixture and the organic layer was washed twice with water, dried over sodium sulfate and concentrated under reduced pressure. The resulting residue was purified by column chromatography to yield the desired product.

Synthesis of dibenzyl 2-(benzyloxyphenoxyphosphonomethyl)pentanedioate

This compound was prepared in a manner similar to that as described above for the synthesis of dibenzyl 2-(benzyloxyhydrophosphorylmethyl)pentanedioate, except phenol is used in place of benzyl alcohol.

Synthesis of 2-O-(phenylphosphonomethyl)pentanedioic acid

A mixture of dibenzyl 2-(benzyloxyphenoxyphosphonomethyl)pentanedioate (1.0 g, 1.8 mmol), palladium on carbon catalyst (10%, 0.5 g) and water (25 ml) was shaken under hydrogen (60 psi) for 16 hours. The reaction mixture was filtered over celite and the filtrate was lyophilized to yield the desired product as grayish-white crystals.

Example 5

A patient is at risk of injury from an ischemic event. The patient may be pretreated with an effective amount of a compound of the present invention. It is expected that after the pretreatment, the patient would be protected from any injury due to the ischemic event.

Example 6

A patient is suffering from an ischemic event. The patient may be administered during the event, or within a 30 minute window after the event, an effective amount of a compound of the present invention. It is expected that after the treatment, the patient would recover or would not suffer any significant injury due to the ischemic event.

Example 7

A patient has suffered injury from an ischemic event. The patient may be administered an effective amount of a compound of the present invention. It is expected that after the treatment, the patient would recover from the injury due to the ischemic event.

Example 8

A patient is suffering from a glutamate abnormality. The patient may then be administered an effective amount of a compound of the present invention. It is expected that after the treatment, the patient would be protected from further injury due to the glutamate abnormality or would recover from the glutamate abnormality.

Example 9

A patient is suffering from or has suffered from a nervous insult, such as that arising from a neurodegenerative disease or a neurodegenerative process. The patient may then be administered an effective amount of a compound of the present invention. It is expected that after the treatment, the patient would be protected from further injury due to the nervous insult or would recover from the nervous insult.

Example 10

A patient is suffering from Parkinson's disease. The patient may then be administered an effective amount of a compound of the present invention. It is expected that after the treatment, the patient would be protected from further neurodegeneration or would recover from Parkinson's disease.

Example 11

A patient is suffering from ALS. The patient may then be administered an effective amount of a compound of the present invention. It is expected that after the treatment, the patient would be protected from further neurodegeneration or would recover from ALS.

Example 12

A patient is suffering from epilepsy. The patient may then be administered an effective amount of a compound of the present invention. It is expected that after the treatment, the patient would be protected from further neurodegeneration or would recover from epilepsy.

Example 13

A patient is suffering from abnormalities in myelination/demyelination processes. The patient may then be administered an effective amount of a compound of the present invention. It is expected that after the treatment, the patient would be protected from further neurodegeneration or would recover from the abnormalities in myelination/demyelination processes.

Example 14

A patient is suffering from or has suffered from a cerebrovascular accident, such as stroke. The patient may then be administered an effective amount of a compound of the present invention. It is expected that after the treatment, the patient would be protected from or would recover from any injury due to the cerebrovascular accident.

Example 15

A patient is suffering from a head trauma. The patient may then be administered an effective amount of a compound of the present invention. It is expected that after the treatment, the patient would be protected from or would recover from any ischemic brain, spinal or peripheral injury resulting from the head trauma.

Example 16

A patient is suffering from a spinal trauma. The patient may then be administered an effective amount of a compound of the present invention. It is expected that after the treatment, the patient would be protected from or would recover from any ischemic injury resulting from the spinal trauma.

Example 17

A patient is about to undergo surgery. The patient may be administered an effective amount of a compound of the present invention. It is expected that after the treatment, the patient would not develop any ischemic brain, spinal or peripheral injury resulting from or associated with the surgery.

Example 18

A patient is suffering from focal ischemia, such as that associated with thromboembolytic occlusion of a cerebral vessel, traumatic head injury, edema or brain tumors. The patient may then be administered an effective amount of a compound of the present invention. It is expected that after the treatment, the patient would be protected from or would recover from any brain, spinal or peripheral injury resulting from the focal ischemia.

Example 19

A patient is suffering from global ischemia. The patient may then be administered an effective amount of a compound of the present invention. It is expected that after the treatment, the patient would be protected from or would recover from any brain, spinal or peripheral injury resulting from the global ischemia.

Example 20

A patient is suffering from a cardiac arrest. The patient may then be administered an effective amount of a compound of the present invention. It is expected that after the treatment, the patient would be protected from or would recover from any ischemic brain, spinal or peripheral injury associated with the cardiac arrest.

Example 21

A patient is suffering from hypoxia, asphyxia or perinatal asphyxia. The patient may then be administered an effective amount of a compound of the present invention. It is expected that after the treatment, the patient would be protected from or would recover from any ischemic brain, spinal or peripheral injury associated with the hypoxia, asphyxia or perinatal asphyxia.

Example 22

A patient is suffering from a cerebro-cortical injury. The patient may then be administered an effective amount of a compound of the present invention. It is expected that after the treatment, the patient would be protected from or would recover from any ischemic brain injury resulting from the cerebro-cortical injury.

Example 23

The patient is suffering from an injury to the caudate nucleus. The patient may then be administered an effective amount of a compound of the present invention. It is expected that after the treatment, the patient would be protected from or would recover from any ischemic brain injury resulting from the injury to the caudate nucleus.

Example 24

A patient is diagnosed with a condition as identified in these examples. An effective amount of a compound of the present invention may then be administered to the patient intravenously, intramuscularly, intraventricularly to the brain, rectally, subcutaneously, intranasally, through a catheter with or without a pump, orally, through a transdermal patch, topically, or through a polymer implant. After the treatment, the patient's condition would be expected to improve.

Example 25

A patient is diagnosed with a condition as identified in these examples. A compound of the present invention may then be administered to the patient in the form of a 100 mg/kg bolus, optionally followed by a 20 mg/kg per hour intravenous infusion over a two-hour period. After the treatment, the patient's condition would be expected to improve.

Example 26

A patient is suffering from a cortical injury due to a condition identified in these examples. The patient may then be administered an effective amount of a compound of the present invention. It is expected that after the treatment, the patient would be protected from further injury, or would exhibit at least 65% to at least 80% recovery from the cortical injury.

Example 27

A patient is suffering from adenocarcinoma of the prostate. The patient may then be administered an effective amount of a compound of the present invention. After this initial treatment, the patient may optionally be administered the same or a different compound of the present invention in intermittent or continuous doses by subdural pump. It is expected that the treatment(s) would prevent recurrences of the adenocarcinoma, or inhibit (i.e., arrest development of) or relieve (i.e., cause regression of) the adenocarcinoma tumor cells.

Example 28

A patient is suffering from adenocarcinoma of the prostate. The patient may then be administered an effective amount of a compound of the present invention by direct injection into the tumor. After this initial treatment, the patient may optionally be administered an effective amount of the same or a different compound of the present invention in intermittent or continuous doses by implantation of a biocompatible polymeric matrix delivery system. It is expected that the treatment(s) would prevent recurrences of the adenocarcinoma, or inhibit (i.e., arrest development of) or relieve (i.e., cause regression of) the adenocarcinoma tumor cells.

Example 29

A patient is diagnosed with benign prostatic hyperplasia. The patient may then be administered an effective amount of a compound of the present invention by direct injection into the tumor. After this initial treatment, the patient may optionally be administered the same or a different compound of the present invention in intermittent or continuous doses by injection, subdural pump or polymeric matrix implant. It is expected that after the treatment (s), the benign prostatic hyperplastic cells would not develop into carcinoma.

Example 30

A patient is suffering from adenocarcinoma of the prostate. The adenocarcinoma does not appear to have metastasized. The patient undergoes surgery to remove the adenocarcinoma. After post-surgical recovery, the patient may be locally administered an effective amount of a compound of the present invention in intermittent or continuous doses by injection, subdural pump or polymeric matrix implant. It is expected that after the treatment, the patient would be protected from recurrences of the adenocarcinoma, and any residual tumorous cells would be inhibited (i.e., arrested in development) or relieved (i.e., caused to regress).

Example 31

A patient is suffering from metastatic adenocarcinoma of the prostate. Although the adenocarcinoma appears to have metastasized, the patient nevertheless undergoes surgery to remove the adenocarcinoma. The patient may then be locally administered an effective amount of a compound of the present invention approximately from the time of initial diagnosis through post-surgical recovery. After post-surgical recovery, the patient may continue the same treatment by a regimen of periodic local administration, and carefully monitored for adverse side-effects. It is expected that after the treatments, the patient would be protected from recurrences of the adenocarcinoma, and any residual tumorous cells would be inhibited (i.e., arrested in development) or relieved (i.e., caused to regress).

Example 32

A patient is suffering from cancer as defined herein. An effective amount of a compound of the present invention may be administered directly to the cancer cells. After this initial treatment, the patient may be optionally administered an effective amount of the same or a different compound of the present invention by direct injection, subdural pump or implantation of a biocompatible polymeric matrix delivery system. It is expected that after the treatment(s), the patient would be protected from recurrences of the cancer, and the cancer would be inhibited (i.e., arrested in development) or relieved (i.e., caused to regress).

The invention being thus described, it will be obvious that the same may be varied in many ways. Such variations are not to be regarded as a departure from the spirit and scope of the invention and all such modifications are intended to be included within the scope of the following claims.

We claim:

1. A compound of formula I:

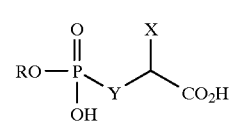

or a pharmaceutically acceptable salt or hydrate thereof, wherein:

Y is $CR_1R_2$;

X is —$(CH_2)_2COOH$;

R, $R_1$ and $R_2$ are independently selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl and Ar, wherein said R, $R_1$ and $R_2$ are independently unsubstituted or substituted with $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino, Ar or mixtures thereof, provided that R is not hydrogen; and Ar is selected from the group consisting of 1-naphthyl, 2-naphthyl, 2-indolyl, 3-indolyl, 2-furyl, 3-furyl, 2-thienyl, 3-thienyl, 2-pyridyl, 3-pyridyl, 4-pyridyl, benzyl and phenyl, wherein said Ar has one to three substituent(s) independently selected from the group consisting of hydrogen, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino and mixtures thereof.

2. The compound of claim 1, wherein Y is $CH_2$.

3. The compound of claim 2, which is selected from the group consisting of:
2-(O-methylphosphonomethyl)pentanedioic acid;
2-(O-ethylphoshonomethyl)pentanedioic acid;
2-(O-propylphoshonomethyl)pentanedioic acid,
2-(O-butylphosphonomethyl)pentanedioic acid;
2-(O-phenylphosphonomethyl)pentanedioic acid;
2-[O-(2-phenylethyl)phosphonometyl]pentanedioic acid;
2-[O-(3-phenylpropyl)phosophonomethyl]pentanedioic acid;
2-[O-(4-pyridyl)phosphonomethyl]pentanedioic acid; and
2-(O-benzylphosphonomethyl)pentanedioic acid.

4. A pharmaceutical composition comprising:
(i) a therapeutically effective amount of the compound of formula I:

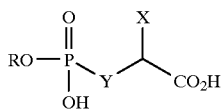

I or a pharmaceutically acceptable salt or hydrate thereof, wherein:
Y is $CR_1R_2$;
X is —$(CH_2)_2COOH$;
R, $R_1$ and $R_2$ are independently selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl and Ar, wherein said R, $R_1$ and $R_2$ are independently unsubstituted or substituted with $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino, Ar or mixtures thereof, provided that R is not hydrogen; and Ar is selected from the group consisting of 1-naphthyl, 2-naphthyl, 2-indolyl, 3-indolyl, 2-furyl, 3-furyl, 2-thienyl, 3-thienyl, 2-pyridyl, 3-pyridyl, 4-pyridyl, benzyl and phenyl, wherein said Ar has one to three substituent(s) independently selected from the group consisting of hydrogen, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino and mixtures thereof; and (ii) a pharmaceutically acceptable carrier.

5. The pharmaceutical composition of claim 4, wherein in said compound, Y is $CH_2$.

6. The pharmaceutical composition of claim 5, wherein said compound is selected from the group consisting of:
2-O-(methylphosphonomethyl)pentanedioic acid;
2-O-(ethylphosphonomethyl)pentanedioic acid;
2-O-(propylphosphonomethyl)pentanedioic acid;
2-(O-butylphosphonomethyl)pentanedioic acid;
2-(O-phenylphosphonomethyl)pentanedioic acid;
2-[O-(2-phenylethyl)phosphonomethyl]pentanedioic acid,
2-[O-(3-phenylpropyl)phosphonomethyl]pentanedioic acid;
2-[O-(4-pyridyl)phosphonomethyl]pentanedioic acid; and
2-(O-benzylphosphonomethyl)pentanedioic acid.

7. The pharmaceutical composition of claim 4, further comprising a therapeutic agent selected from the group consisting of therapeutic hormones, chemotherapeutic agents, monoclonal antibodies, anti-angiogenesis agents, radiolabelled compounds, antineoplastic agents and mixtures thereof.

8. The pharmaceutical composition of claim 4, wherein said compound is present in an amount that is effective for inhibiting NAALADase activity in an animal, treating a glutamate abnormality in an animal or treating a prostate disease in an animal.

9. A method of inhibiting NAALADase enzyme activity in an animal, comprising administering to said animal an effective amount of the compound of formula I:

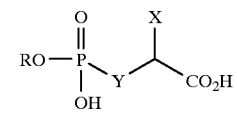

I or a pharmaceutically acceptable salt or hydrate thereof, wherein:
Y is $CR_1R_2$;
X is selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl and Ar, wherein said X is unsubstituted or substituted with carboxy, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino, Ar or mixtures thereof;

R, $R_1$ and $R_2$ are independently selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl and Ar, wherein said R, $R_1$ and $R_2$ are independently unsubstituted or substituted with $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino, Ar or mixtures thereof, provided that R is not hydrogen when X is carboxymethyl or carboxyethyl; and Ar is selected from the group consisting of 1-naphthyl, 2-naphthyl, 2-indolyl, 3-indolyl, 2-furyl, 3-furyl, 2-thienyl, 3-thienyl, 2-pyridyl, 3-pyridyl, 4-pyridyl, benzyl and phenyl, wherein said Ar has one to three substituent(s) independently selected from the group consisting of hydrogen, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino and mixtures thereof.

10. The method of claim 9, wherein in said compound, Y is $CH_2$.

11. The method of claim 10, wherein in said compound, R is hydrogen.

12. The method of claim 11, wherein said compound is selected from the group consisting of:

phosphonopropanoic acid;
2-methyl-3-phosphonopropanoic acid;
2-ethyl-3-phosphonopropanoic acid;
2-propyl-3-phosphonopropanoic acid;
2-butyl-3-phosphonopropanoic acid;
2-phenyl-3-phosphonopropanoic acid;
2-(2-phenylethyl)-3-phosphonopropanoic acid;
2-(3-phenylpropyl)-3-phosphonopropanoic acid;
2-(4-pyridyl)-3-phosphonopropanoic acid; and
2-benzyl-3-phosphonopropanoic acid.

13. The method of claim 10, wherein in said compound, X is substituted with carboxy.

14. The method of claim 13, wherein in said compound, X is carboxyethyl.

15. The method of claim 14, wherein said compound is selected from the group consisting of:

2-(O-methylphosphonomethyl)pentanedioic acid;
2-(O-ethylphosphonomethyl)pentanedioic acid;
2-(O-propylphosphonomethyl)pentanedioic acid;
2-(O-butylphosphonomethyl)pentanedioic acid;
2-(O-phenylphosphonomethyl)pentanedioic acid;
2-[O-(2-phenylethyl)phosphonomethyl]pentanedioic acid;
2-[O-(3-phenylpropyl)phosphonomethyl]pentanedioic acid;
2-[O-(4-pyridyl)phosphonomethyl]pentanedioic acid; and
2-(O-benzylphosphonomethyl)pentanedioic acid.

16. A method of treating a glutamate abnormality in an animal, comprising administering to said animal an effective amount of a compound of formula I:

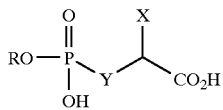

I or a pharmaceutically acceptable salt or hydrate thereof, wherein:

Y is selected from the group consisting of $CR_1R_2$, $NR_3$ and O;

X is selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl and Ar, wherein said X is unsubstituted or substituted with carboxy, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino, Ar or mixtures thereof;

R, $R_1$, $R_2$ and $R_3$ are independently selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl and Ar, wherein said R, $R_1$, $R_2$ and $R_3$ are independently unsubstituted or substituted with $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino, Ar or mixtures thereof, provided that R is not hydrogen when X is carboxymethyl or carboxyethyl; and Ar is selected from the group consisting of 1-naphthyl, 2-naphthyl, 2-indolyl, 3-indolyl, 2-furyl, 3-furyl, 2-thienyl, 3-thienyl, 2-pyridyl, 3-pyridyl, 4-pyridyl, benzyl and phenyl, wherein said Ar has one to three substituent(s) independently selected from the group consisting of hydrogen, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino and mixtures thereof.

17. The method of claim 16, wherein in said compound, Y is $CH_2$.

18. The method of claim 17, wherein is said compound, R is hydrogen.

19. The method of claim 18, wherein said compound is selected from the group consisting of:

phosphonopropanoic acid;
2-methyl-3-phosphonopropanoic acid;
2-ethyl-3-phosphonopropanoic acid;
2-propyl-3-phosphonopropanoic acid;
2-butyl-3-phosphonopropanoic acid;
2-phenyl-3-phosphonopropanoic acid;
2-(2-phenylethyl)-3-phosphonopropanoic acid;
2-(3-phenylpropyl)-3-phosphonopropanoic acid;
2-(4-pyridyl)-3-phosphonopropanoic acid; and
2-benzyl-3-phosphonopropanoic acid.

20. A method of treating a glutamate abnormality in an animal, comprising administering to said animal an effective amount of a compound of formula I:

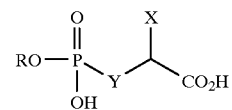

I or a pharmaceutically acceptable salt or hydrate thereof, wherein in said compound:

Y is $CH_2$;

X is selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl and Ar, wherein said X is substituted with carboxy;

R, $R_1$, $R_2$ and $R_3$ are independently selected from the group consisting of hydrogen, $C_1$–$C_9$ straight or branched chain alkyl, $C_2-C_9$ straight or branched chain alkenyl, $C_3-C_8$ cycloalkyl, $C_5-C_7$ cycloalkenyl and Ar, wherein said R, $R_1$, $R_2$ and $R_3$ are independently unsubstituted or substituted with $C_3-C_8$ cycloalkyl, $C_5-C_7$ cycloalkenyl, halo, hydroxy, nitro, trifluoromethyl, $C_1-C_6$ straight or branched chain alkyl, $C_2-C_6$ straight or branched chain alkenyl, $C_1-C_4$ alkoxy, $C_2-C_4$ alkenyloxy, phenoxy, benzyloxy, amino, Ar or mixtures thereof, provided that R is not hydrogen when X is carboxymethyl or carboxyethyl; and Ar is selected from the group consisting of 1-naphthyl, 2-naphthyl, 2-indolyl, 3-indolyl, 2-furyl, 3-furyl, 2-thienyl, 3-thienyl, 2-pyridyl, 3-pyridyl, 4-pyridyl, benzyl and phenyl, wherein said Ar has one to three substituent(s) independently selected from the group consisting of hydrogen, halo, hydroxy, nitro, trifluoromethyl, $C_1-C_6$ straight or branched chain alkyl, $C_2-C_6$ straight or branched chain alkenyl, $C_1-C_4$ alkoxy, $C_2-C_4$ alkenyloxy, phenoxy, benzyloxy, amino and mixtures thereof, wherein in said compound Y is $CH_2$ and X is substituted with carboxy.

21. The method of claim 20, wherein in said compound, X is carboxyethyl.

22. The method of claim 21, wherein said compound is selected from the group consisting of:
2-(O-methylphosphonomethyl)pentanedioic acid;
2-(O-ethylphosphonomethyl)pentanedioic acid;
2-(O-propylphosphonomethyl)pentanedioic acid;
2-(O-butylphosphonomethyl)pentanedioic acid;
2-(O-phenylphosphonomethyl)pentanedioic acid;
2-[O-(2-phenylethyl)phosphonomethyl]pentanedioic acid;
2-[O-(3-phenylpropyl)phosphonomethyl]pentanedioic acid;
2-[O-(4-pyridyl)phosphonomethyl]pentanedioic acid; and
2-(O-benzylphosphonomethyl)pentanedioic acid.

23. The method of claim 16, wherein said glutamate abnormality is selected from the group consisting of epilepsy, Alzheimer's disease, Parkinson's Disease, Amyotrophic Lateral Sclerosis (ALS), Huntington's Disease, schizophrenia, chronic pain, and neuronal insult.

24. The method of claim 16, wherein said glutamate abnormality is ischemia.

25. A method of treating a prostate disease in an animal, comprising administering to said animal an effective amount of a compound of formula I:

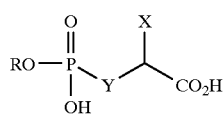

or a pharmaceutically acceptable salt or hydrate thereof, wherein:
Y is $CR_1R_2$;
X is selected from the group consisting of hydrogen, $C_1-C_9$ straight or branched chain alkyl, $C_2-C_9$ straight or branched chain alkenyl, $C_3-C_8$ cycloalkyl, $C_5-C_7$ cycloalkenyl and Ar, wherein said X is unsubstituted or substituted with carboxy, $C_3-C_8$ cycloalkyl, $C_5-C_7$ cycloalkenyl, halo, hydroxy, nitro, trifluoromethyl, $C_1-C_6$ straight or branched chain alkyl, $C_2-C_6$ straight or branched chain alkenyl, $C_1-C_4$ alkoxy, $C_2-C_4$ alkenyloxy, phenoxy, benzyloxy, amino, Ar or mixtures thereof;

R, $R_1$ and $R_2$ are independently selected from the group consisting of hydrogen, $C_1-C_9$ straight or branched chain alkyl, $C_2-C_9$ straight or branched chain alkenyl, $C_3-C_8$ cycloalkyl, $C_5-C_7$ cycloalkenyl and Ar, wherein said R, $R_1$ and $R_2$ are independently unsubstituted or substituted with $C_3-C_8$ cycloalkyl, $C_5-C_7$ cycloalkenyl, halo, hydroxy, nitro, trifluoromethyl, $C_1-C_6$ straight or branched chain alkyl, $C_2-C_6$ straight or branched chain alkenyl, $C_1-C_4$ alkoxy, $C_2-C_4$ alkenyloxy, phenoxy, benzyloxy, amino, Ar or mixtures thereof, provided that R is not hydrogen when X is carboxymethyl or carboxyethyl; and Ar is selected from the group consisting of 1-naphthyl, 2-naphthyl, 2-indolyl, 3-indolyl, 2-furyl, 3-furyl, 2-thienyl, 3-thienyl, 2-pyridyl, 3-pyridyl, 4-pyridyl, benzyl and phenyl, wherein said Ar has one to three substituent(s) independently selected from the group consisting of hydrogen, halo, hydroxy, nitro, trifluoromethyl, $C_1-C_6$ straight or branched chain alkyl, $C_2-C_6$ straight or branched chain alkenyl, $C_1-C_4$ alkoxy, $C_2-C_4$ alkenyloxy, phenoxy, benzyloxy, amino and mixtures thereof.

26. The method of claim 25, wherein in said compound, Y is $CH_2$.

27. The method of claim 26, wherein in said compound, R is hydrogen.

28. The method of claim 27, wherein said compound is selected from the group consisting of:
phosphonopropanoic acid;
2-methyl-3-phosphonopropanoic acid;
2-ethyl-3-phosphonopropanoic acid;
2-propyl-3-phosphonopropanoic acid;
2-butyl-3-phosphonopropanoic acid;
2-phenyl-3-phosphonopropanoic acid;
2-(2-phenylethyl)-3-phosphonopropanoic acid;
2-(3-phenylpropyl)-3-phosphonopropanoic acid;
2-(4-pyridyl)-3-phosphonopropanoic acid; and
2-benzyl-3-phosphonopropanoic acid.

29. The method of claim 26, wherein in said compound, X is substituted with carboxy.

30. The method of claim 29, wherein in said compound, X is carboxyethyl.

31. The method of claim 30, wherein said compound is selected from the group consisting of:
2-(O-methylphosphonomethyl)pentanedioic acid;
2-(O-ethylphosonomethyl)pentanedoic acid;
2-(O-propylphosphonomethyl)pentanedioic acid;
2-(O-butylphosphonomethyl)pentanedioic acid;
2-(O-phenylphosphonomethyl)pentanedioic acid;
2-[O-(2-phenylethyl)phosphonomethyl]pentanedioic acid;
2-[O-(3-phenylpropyl)phosphonomethyl]pentanedioic acid;
2-[O-(4-pyridyl)phosphonomethyl]pentanedioic acid; and
2-(O-benzylphosphonomethyl)pentanedioic acid.

32. The method of claim 25, wherein said prostate disease is prostate cancer or benign prostatic hyperplasia.

33. The method of claim 16, wherein said glutamate abnormality is stroke.

* * * * *

UNITED STATES PATENT AND TRADEMARK OFFICE
CERTIFICATE OF CORRECTION

Page 1 of 2

PATENT NO. : 6,054,444
DATED     : April 25, 2000
INVENTOR(S) : Paul F. JACKSON et al.

It is certified that error appears in the above-identified patent and that said Letters Patent is hereby corrected as shown below:

Claim 3, column 33, line 31, please replace
"2-[O-(2-phenylethyl)phosphonometyl]pentanedioic acid"
with --2-[O-(2-phenylethyl)phosphonomethyl]pentanedioic acid--.

Claim 3, column 33, line 32, please replace
"2-[O-(3-phenylpropyl)phosophonomethyl]pentanedioic"
with --2-[O-(3-phenylpropyl)phosphonomethyl]pentanedioic--.

Claim 6, column 34, line 11, please replace
"2-O-(methylphosphonomethyl)pentanedioic"
with --2-(O-methylphosphonomethyl)pentanedioic--.

Claim 6, column 34, line 12, please replace
"2-O-(ethylphosphonomethyl)pentanedioic"
with --2-(O-ethylphosphonomethyl)pentanedioic--.

Claim 6, column 34, line 13, please replace
"2-O-(propylphosphonomethyl)pentanedioic"
with --2-(O-propylphosphonomethyl)pentanedioic--.

Claim 18, column 36, line 31, after "wherein" and before "said compound,", please replace "is" with --in--.

UNITED STATES PATENT AND TRADEMARK OFFICE
CERTIFICATE OF CORRECTION

PATENT NO. : 6,054,444
DATED : April 25, 2000
INVENTOR(S) : Paul F. Jackson, et. al.

It is certified that error appears in the above-identified patent and that said Letters Patent is hereby corrected as shown below:

Claim 31, column 38, line 50, please replace
"2-(O-ethylphosonomethyl)pentaned oic"
with --2-(O-ethylphosphonomethyl)pentanedioic--.

Signed and Sealed this

Twenty-seventh Day of February, 2001

Attest:

NICHOLAS P. GODICI

Attesting Officer

Acting Director of the United States Patent and Trademark Office